United States Patent
Hornsperger et al.

(10) Patent No.: US 10,870,623 B2
(45) Date of Patent: Dec. 22, 2020

(54) TRIFLUOROMETHYLPROPANAMIDE DERIVATIVES AS HTRA1 INHIBITORS

(71) Applicant: Hoffmann-La Roche Inc., Little Falls, NJ (US)

(72) Inventors: Benoit Hornsperger, Altkirch (FR); Hans Peter Maerki, Basel (CH); Peter Mohr, Basel (CH); Michael Reutlinger, Freiburg (DE); Markus Rudolph, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/283,640

(22) Filed: Feb. 22, 2019

(65) Prior Publication Data

US 2019/0185426 A1  Jun. 20, 2019

Related U.S. Application Data

(63) Continuation of application No. PCT/EP2017/071019, filed on Aug. 21, 2017.

(30) Foreign Application Priority Data

Aug. 23, 2016 (EP) .................................. 16185356

(51) Int. Cl.
| | | |
|---|---|---|
| *C07D 401/12* | (2006.01) | |
| *C07D 403/12* | (2006.01) | |
| *C07D 207/12* | (2006.01) | |
| *C07D 409/12* | (2006.01) | |

(52) U.S. Cl.
CPC ......... *C07D 207/12* (2013.01); *C07D 401/12* (2013.01); *C07D 403/12* (2013.01); *C07D 409/12* (2013.01)

(58) Field of Classification Search
CPC .. C07D 401/12; C07D 403/13; C07D 207/12; C07D 403/12
See application file for complete search history.

(56) References Cited

U.S. PATENT DOCUMENTS

| | | |
|---|---|---|
| 9,980,929 B2 | 5/2018 | Hornsperger et al. |
| 10,428,108 B2 | 10/2019 | Hornsperger et al. |
| 2005/0027101 A1 | 2/2005 | Gutheil et al. |

FOREIGN PATENT DOCUMENTS

| | | |
|---|---|---|
| WO | 96/02499 A1 | 2/1996 |
| WO | 99/07734 A2 | 2/1999 |
| WO | 00/61542 A1 | 10/2000 |
| WO | 2005/035525 A2 | 4/2005 |
| WO | 2008/101160 A2 | 8/2008 |
| WO | 2012/093101 A1 | 7/2012 |
| WO | 2014/002053 A1 | 1/2014 |
| WO | 2016/135070 A1 | 9/2016 |
| WO | 2016/180751 A1 | 11/2016 |

OTHER PUBLICATIONS

Perni et al., Bioorganic & Medicinal Chemistry Letters, 14, 2004, pp. 1441-1446. (Year: 2004).*
Cregge et al., "Inhibition of Human Neutrophil Elastase. 4. Design, Synthesis, X-ray Crystallographic Analysis, and Structure-Activity Relationships for a Series of P2-Modified, Orally Active Peptidyl Pentafluoroethyl Ketones" Journal of Medicinal Chemistry 41:2451-2480 (1998).
"International Preliminary Report on Patentability—PCT/EP2017/071019":pp. 1-8 (dated Mar 7, 2019).
"International Search Report—PCT/EP2017/071019":pp. 1-8 (dated Sep 27, 2017).
Perni et al., "Inhibitors of hepatitis C virus NS3.4A protease 2. Warhead SAR and optimization" Bioorganic & Medicinal Chemistry Letters 14(6):1441-1446 (2004).
Ammar, M., et al., "What's Ahead for the Treatment of Dry AMD" Review Ophthalmology 27(3):60-65 (Mar. 7, 2020) https://www.reviewofophthalmology.com/artivle/whats-ahead-for-the-treatment-of-dry-amd.
Bernstein, Peter R. et al., "Examination of Peptidic alpha-beta Diamino-alpha-difluoroketones as Inhibitors of human Leukocyte Elastase" Bioorganic and Medicinal Chemistry Letters (XP002768444), 4(18):2175-2178 (Oct. 1, 1994).
Derstine, C., et al., CAS Registry Database, 182001-67-8, 1996:494556 (Trifluoromethyl-Substituted Imidazolines: Novel Precursors of Trifluoromethyl Ketones Amenable to Peptide Synthesis), pgs. 1Other Date Nov. 13, 2019.
Doherty A. M. et al., "Design and Synthesis of Potent, Selective, and Orally Active Fluorine-Containing Renin Inhibitors" Journal of Medicinal Chemistry (XP002768443), 35:2-14 (Jan. 1, 1992).
Giovani, Simone et al., "Plasmodium falciparum subtilisin-like protease 1: discovery of potent difluorostatone-based inhibitors" RSC Advances (XP002768447), 5:22431-22448 (Feb. 19, 2015).
He, M., et al., "The Association Between Diabetes and Age-Related Macular Degeneration Among the Elderly in Taiwan" Diabetes Care 41:2202-2211 (Oct. 1, 2018).
International Preliminary Report on Patentability (IPRP) for PCT/EP2017/067519 dated Jan. 22, 2019.

(Continued)

*Primary Examiner* — Laura L Stockton
(74) *Attorney, Agent, or Firm* — Bradley E. Davis

(57) ABSTRACT

The invention provides novel compounds having the general formula (I)

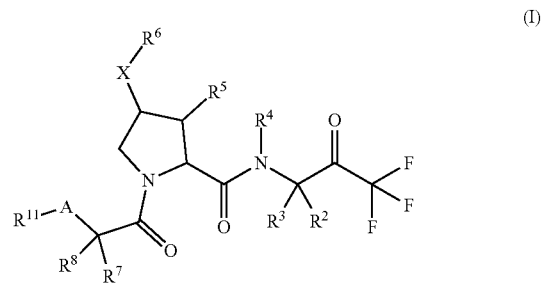

wherein $R^2$, $R^3$, $R^4$, $R^5$, $R^6$, $R^7$, $R^8$, X, A and $R^{11}$ are as described herein, compositions including the compounds and methods of using the compounds.

28 Claims, No Drawings

(56) References Cited

OTHER PUBLICATIONS

International Search Report for PCT/EP2017/067519 dated Aug. 14, 2017.
ISR and Written Opinion for PCT/EP2017/054677 (dated Jul. 4, 2017).
ISR and Written Opinion for PCT/EP2017/054682 (dated May 4, 2017).
Jacobo, Sarah Melissa P. et al., "Focus on Molecules: HtrA1 and neovascular AMD" Experimental Eye Research (XP028884160), 94(1):4-5 (2012).
Knobbe, C., et al., "Macular degeneration prevention" All About Vision (Article retrieved from webpage: May 11, 2020; Last Update posted: Oct. 16, 2016),:1-12 (May 11, 2020) https://www.allaboutvision.com/conditions/amd-prevention.htm.
Sasubilli, Ramakrishna et al., "General Inverse Solid-Phase Synthesis Method for C-Terminally Modified Peptide Mimetics" Journal of Combinatorial Chemistry (XP002522469), 6(6):911-915 (Nov. 1, 2014).
Skiles et al., "Inhibition of human leukocyte elastase by N-substituted peptides containing a,a-Difluorostatone residues at P1" J. Med. Chem. 35:4795-4808 (1992).
Truebestein et al., "Substrate-induced remodeling of the active site regulates human HTRA1 activity" Nat. Struct. Mol. Biol. 18(3):386-388 (Feb. 6, 2011).

\* cited by examiner

TRIFLUOROMETHYLPROPANAMIDE DERIVATIVES AS HTRA1 INHIBITORS

CROSS-REFERENCE TO RELATED APPLICATIONS

This application is a continuation of International Application No. PCT/EP2017/071019, filed on Aug. 21, 2017, which claims priority to European Patent Application No. 16185356.9, filed on Aug. 23, 2016, the contents of which are incorporated herein by reference in their entireties.

The present invention relates to organic compounds useful for therapy or prophylaxis in a mammal, and in particular to serine protease HtrA1 inhibitors for the treatment or prophylaxis of HtrA1-mediated ocular diseases, such as wet or dry age-related macular degeneration, geographic atrophy, diabetic retinopathy, retinopathy of prematurity and polypoidal choroidal vasculopathy.

The present invention provides novel compounds of formula (I)

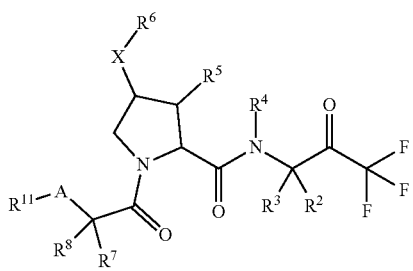

wherein
$R^2$, $R^3$, $R^4$, $R^5$ and $R^7$ are independently selected from
  i) H,
  ii) $C_{1-6}$-alkyl, and
  iii) $C_{3-8}$-cycloalkyl;
X is selected from
  i) —O—,
  ii) —S—, and
  iii) —S(O)$_2$—;
$R^6$ is selected from
  i) aryl substituted with $R^{12}$, $R^{13}$ and $R^{14}$,
  i) aryl-$C_{1-6}$-alkyl substituted with $R^{12}$, $R^{13}$ and $R^{14}$,
  ii) heteroaryl substituted with $R^{12}$, $R^{13}$ and $R^{14}$, and
  iii) heteroaryl-$C_{1-6}$-alkyl substituted with $R^{12}$, $R^{13}$ and $R^{14}$;
A is selected from
  i) —O—,
  ii) —CH$_2$—,
  iii) —S(O)$_2$NR$^{10}$— and
  iv) —C(O)NR$^{10}$—;
$R^8$ is selected from
  i) H, and
  ii) —CH$_2$R$^9$;
$R^9$ is selected from
  i) H, and
  ii) hydroxy,
  iii) amino-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
  iv) aminocarbonyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
  v) aminocarbonyl-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
  vi) carboxy,
  vii) carboxy-$C_{1-6}$-alkyl,
  viii) $C_{1-6}$-alkoxy,
  ix) $C_{1-6}$-haloalkoxy,
  x) $C_{1-6}$-alkoxycarbonyl,
  xi) $C_{1-6}$-alkoxycarbonyl-$C_{1-6}$-alkyl,
  xii) $C_{3-8}$-cycloalkyl,
  xiii) aryl substituted with $R^{15}$, $R^{16}$ and $R^{17}$,
  xiv) aryl-$C_{1-6}$-alkyl substituted with $R^{15}$, $R^{16}$ and $R^{17}$,
  xv) aryl-$C_{1-6}$-alkoxy substituted with $R^{15}$, $R^{16}$ and $R^{17}$,
  xvi) heteroaryl substituted with $R^{15}$, $R^{16}$ and $R^{17}$,
  xvii) heteroaryl-$C_{1-6}$-alkyl substituted with $R^{15}$, $R^{16}$ and $R^{17}$, and
  xviii) heteroaryl-$C_{1-6}$-alkoxy substituted with $R^{15}$, $R^{16}$ and $R^{17}$
  xix) heterocycloalkyl substituted with $R^{15}$, $R^{16}$ and $R^{17}$,
  xx) heterocycloalkyl-$C_{1-6}$-alkyl substituted with $R^{15}$, $R^{16}$ and $R^{17}$,
  xxi) heterocycloalkyl-$C_{1-6}$-alkoxy substituted with $R^{15}$, $R^{16}$ and $R^{17}$, and
  xxii) $C_{1-6}$-alkylsilyloxy;
$R^1$ is selected from
  i) amino-$C_{1-6}$-alkyl substituted on the nitrogen atom by $R^{21}$ and $R^{22}$,
  ii) $C_{3-8}$-cycloalkyl substituted with $R^{18}$, $R^{19}$ and $R^{20}$,
  iii) $C_{3-8}$-cycloalkyl-$C_{1-6}$-alkyl substituted with $R^{18}$, $R^{19}$ and $R^{20}$,
  iv) $C_{3-8}$-cycloalkyl(halo)-$C_{1-6}$-alkyl substituted with $R^{18}$, $R^{19}$ and $R^{20}$,
  v) aryl substituted with $R^{18}$, $R^{19}$ and $R^{20}$,
  vi) aryl-$C_{1-6}$-alkyl substituted with $R^{18}$, $R^{19}$ and $R^{20}$,
  vii) aryl-$C_{3-8}$-cycloalkyl substituted with $R^{18}$, $R^{19}$ and $R^{20}$,
  viii) aryl-heterocycloalkyl substituted with $R^{18}$, $R^{19}$ and $R^{20}$
  ix) aryl(halo)-$C_{1-6}$-alkyl substituted with $R^{18}$, $R^{19}$ and $R^{20}$,
  x) aryl(halo)-$C_{3-8}$-cycloalkyl substituted with $R^{18}$, $R^{19}$ and $R^{20}$,
  xi) aryl(halo)-heterocycloalkyl substituted with $R^{18}$, $R^{19}$ and $R^{20}$,
  xii) aryloxy-$C_{1-6}$-alkyl substituted with $R^{18}$, $R^{19}$ and $R^{20}$,
  xiii) aryloxy-$C_{3-8}$-cycloalkyl substituted with $R^{18}$, $R^{19}$ and $R^{20}$,
  xiv) aryloxy-heterocycloalkyl substituted with $R^{18}$, $R^{19}$ and $R^{20}$,
  xv) aryloxy(halo)-$C_{3-8}$-cycloalkyl substituted with $R^{18}$, $R^{19}$ and $R^{20}$,
  xvi) aryloxy(halo)-heterocycloalkyl substituted with $R^{18}$, $R^{19}$ and $R^{20}$
  xvii) aryloxy(halo)-$C_{1-6}$-alkyl,
  xviii) heterocycloalkyl substituted with $R^{18}$, $R^{19}$ and $R^{20}$, xix) heterocycloalkyl-$C_{1-6}$-alkyl substituted with $R^{18}$, $R^{19}$ and $R^{20}$,
xx) heterocycloalkyl-$C_{3-8}$-cycloalkyl substituted with $R^{18}$, $R^{19}$ and $R^{20}$,
xxi) heterocycloalkyl(halo)-$C_{3-8}$-cycloalkyl substituted with $R^{18}$, $R^{19}$ and $R^{20}$,
xxii) heterocycloalkyl(halo)-$C_{1-6}$-alkyl substituted with $R^{18}$, $R^{19}$ and $R^{20}$,
xxiii) heteroaryl substituted with $R^{18}$, $R^{19}$ and $R^{20}$,
xxiv) heteroaryl-$C_{1-6}$-alkyl substituted with $R^{18}$, $R^{19}$ and $R^{20}$,
xxv) heteroaryl-$C_{3-8}$-cycloalkyl substituted with $R^{18}$, $R^{19}$ and $R^{20}$,
xxvi) heteroaryl(halo)-$C_{3-8}$-cycloalkyl substituted with $R^{18}$, $R^{19}$ and $R^{20}$,
xxvii) heteroaryl(halo)-$C_{1-6}$-alkyl substituted with $R^{18}$, $R^{19}$ and $R^{20}$,
xxviii) heteroaryloxy-$C_{1-6}$-alkyl substituted with $R^{18}$, $R^{19}$ and $R^{20}$,
xxix) heteroaryloxy-$C_{3-8}$-cycloalkyl substituted with $R^{18}$, $R^{19}$ and $R^{20}$,
xxx) heteroaryloxy(halo)-$C_{3-8}$-cycloalkyl substituted with $R^{18}$, $R^{19}$ and $R^{20}$, and
xxxi) heteroaryloxy(halo)-$C_{1-6}$-alkyl substituted with $R^{18}$, $R^{19}$ and $R^{20}$;
$R^{12}$, $R^{13}$, $R^{14}$, $R^{15}$, $R^{16}$, $R^{17}$, $R^{18}$, $R^{19}$ and $R^{20}$ are independently selected from
  i) H,
  ii) cyano,
  iii) halogen,
  iv) oxo,
  v) $C_{1-6}$-alkyl,
  vi) amino substituted on the nitrogen atom by two substituents independently selected from H, $C_{1-6}$-alkyl, $C_{1-6}$-alkoxycarbonyl, arylcarbonyl and heteroarylcarbonyl,
  vii) amino-$C_{1-6}$-alkyl substituted on the nitrogen atom by two substituents independently selected from H, $C_{1-6}$-alkyl, $C_{1-6}$-alkoxycarbonyl, arylcarbonyl and heteroarylcarbonyl,
  viii) $C_{1-6}$-alkyl,
  ix) halo-$C_{1-6}$-alkyl,
  x) $C_{3-8}$-cycloalkyl,
  xi) $C_{1-6}$-alkoxycarbonyl-$C_{1-6}$-alkyl,
  xii) carboxy-$C_{1-6}$-alkyl,
  xiii) $C_{1-6}$-alkoxycarbonyl-$C_{1-6}$alkylaminocarbonyl-$C_{1-6}$ alkyl,
  xiv) carboxy-$C_{1-6}$-alkylaminocarbonyl-$C_{1-6}$alkyl,
  xv) $C_{1-6}$-alkoxy,
  xvi) halo-$C_{1-6}$-alkoxy,
  xvii) $C_{1-6}$-alkoxycarbonyl-$C_{1-6}$-alkoxy,
  xviii) carboxy-$C_{1-6}$-alkoxy,
  xix) $C_{1-6}$-alkoxycarbonyl-$C_{1-6}$-alkylaminocarbonyl-$C_{1-6}$-alkoxy,
  xx) carboxy-$C_{1-6}$-alkylaminocarbonyl-$C_{1-6}$-alkoxy, and
  xxi) heterocycloalkyl;
$R^{21}$ and $R^{22}$ are independently selected from
  i) H,
  ii) $C_{1-6}$-alkoxycarbonyl,
  iii) carboxy-$C_{1-6}$-alkyl,
  iv) arylcarbonyl, and
  v) heteroarylcarbonyl;
or pharmaceutically acceptable salts;
with the proviso that N-[(1S)-1-[[(1S)-1-[(2S,4R)-4-benzyloxy-2-[(1-ethyl-3,3,3-trifluoro-2-oxo-propyl)carbamoyl]pyrrolidine-1-carbonyl]-2-methyl-propyl]carbamoyl]-2-methyl-propyl]pyrazine-2-carboxamide is excluded.

Inhibition of the serine protease HtrA1, which belongs to an evolutionarily conserved family of HtrA proteins, has the potential to protect and treat tissue damage caused by the degeneration of retinal or photoreceptor cells in the human eye. The pathophysiological relevance of HtrA1 in the progression of the age-related macular degeneration has been firmly established by human genetic studies where a SNP in the HtrA1 promoter region results in increased HtrA1 transcript and protein levels. Age-related macular degeneration is the leading cause of severe irreversible central vision loss and blindness in individuals over 65 years of age in developed countries. There are two forms of AMD: dry AMD and wet AMD. Wet AMD (also known as exudative AMD), is associated with pathologic posterior choroidal neovascularization subsequent to the disruption of the delimiting Bruch's membrane. Tissue edema due to the leakage from the abnormal blood vessels damages the macula and impairs vision, eventually leading to blindness. In dry AMD, drusen have been reported in the macula of the eye, the cells in the macula die for the progressive accumulation of the drusen, resulting in progressive vision loss. Dry AMD is clinically described to occur in three stages: 1) early, 2) intermediate, and 3) advanced dry AMD. Dry AMD can also progress into wet AMD during any stage of the disease. Treatment strategies for wet AMD exists and the current standard of care is Lucentis (Genentech/Roche) and Eylea (Regeneron), an anti-VEGF antibody and an anti-VEGF trap injected intravitreally respectively. There are no current treatments for preventing loss of vision for the dry form and for preventing progression of dry AMD to local atrophy of the retinal tissue. As discussed above, HtrA1 risk alleles have been associated, with high statistical significance, with the AMD onsets and the protein has been reported to be present in drusen. These studies and further evidences provide relevance that HtrA1 is a fundamental factor involved in the pathophysiology and progression in AMD. This concept is further confirmed in different AMD disease models, where increased HtrA1 protein levels in the retina tissue have been shown to be responsible for the degradation of extracellular matrix (ECM) proteins like fibronectin, fibulins and aggrecan. The physiological balance between production and disintegration of the ECM components allows for both creation and maintenance of proper retina tissue architecture. Such balance has been reported to be lost in the progression of the age-related macular degeneration. In particular, the fibulins (mainly-3, -5, -6) have been reported to be important components of the Bruch's membrane in maintaining the integrity of elastic lamina and organization of the retina tissue overall. Several variants in fibulin 5 and fibulin 3 were reported to be associated with AMD. Missense mutations of the fibulin 5 gene have been associated with reduced secretion of fibulin 5. Different studies have reported that HtrA1 protease activity is directed to the cleavage of the fibulins as substrates. A direct inhibition of HtrA1 protease activity is expected to provide a protection reducing degradation of extracellular matrix proteins, in particular fibulins and fibronectin, therefore preserving the retina tissue structure. The relevance of HtrA1's role in maintenance of the physiological homeostasis of the ECM components is firmly provided by the identification of human loss-of-function mutations causing familial ischemic cerebral small-vessel disease. The molecular mechanism underlies in the deficient TGFbeta inhibition by HtrA1 resulting in increased signaling levels, which in conjunction with deficient HtrA1-mediated degradation of various extracellular matrix components determine thickening of the intima responsible for the ischemic small-vessels. Given its fundamental role in regulating intracellular signaling pathways (e.g. TGFbeta) and the regulation of ECM proteins turnover, HtrA1 has been involved in several pathologies, as ocular diseases, rheumatoid arthritis, osteoarthritis, Alzheimer's disease, and some types of cancer.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of HtrA1, particularly in the treatment or prophylaxis of wet or dry age-related macular degeneration, geographic atrophy, diabetic retinopathy, retinopathy of prematurity and polypoidal choroidal vasculopathy.

The term "amino" denotes a —NH$_2$ group.

The term "amino-C$_{1-6}$-alkyl" denotes an C$_{1-6}$-alkyl group wherein one of the hydrogen atoms of the C$_{1-6}$-alkyl group has been replaced by an amino group. Examples of amino-C$_{1-6}$-alkyl groups are aminomethyl, aminoethyl or aminopropyl. Particular examples of amino-C$_{1-6}$-alkyl is aminomethyl.

The term "aminocarbonyl" denotes a group of the formula —C(O)—R', wherein R' is an amino group.

The term "aminocarbonyl-C$_{1-6}$-alkyl" denotes an C$_{1-6}$-alkyl group wherein one of the hydrogen atoms of the C$_{1-6}$-alkyl group has been replaced by an aminocarbonyl group. Examples of aminocarbonyl-C$_{1-6}$-alkyl groups are aminocarbonylmethyl, aminocarbonylethyl or aminocarbonylpropyl The term "C$_{1-6}$-alkoxy" denotes a group of the formula —O—R', wherein R' is an C$_{1-6}$-alkyl group. Examples of C$_{1-6}$-alkoxy groups include methoxy, ethoxy, n-propoxy, isopropoxy, n-butoxy, isobutoxy and tert-butoxy. Particular example is methoxy.

The term "C$_{1-6}$-alkoxycarbonyl" denotes a group of the formula —C(O)—R', wherein R' is a C$_{1-6}$-alkoxy group. Particular example of C$_{1-6}$-alkoxycarbonyl is a group wherein R' is tert-butoxy.

The term "C$_{1-6}$-alkoxycarbonyl-C$_{1-6}$-alkoxy" denotes an C$_{1-6}$-alkoxy group wherein one of the hydrogen atoms of the C$_{1-6}$-alkoxy group has been replaced by a C$_{1-6}$-alkoxycarbonyl group. Particular example of C$_{1-6}$-alkoxycarbonyl-C$_{1-6}$-alkoxy is a methoxy wherein one of the hydrogen atoms has been replaced by tert-butoxycarbonyl.

The term "C$_{1-6}$-alkoxycarbonyl-C$_{1-6}$-alkyl" denotes an C$_{1-6}$-alkyl group wherein one of the hydrogen atoms of the C$_{1-6}$-alkyl group has been replaced by a C$_{1-6}$-alkoxycarbonyl group. Particular example of C$_{1-6}$-alkoxycarbonyl-C$_{1-6}$-alkyl is a methyl wherein one of the hydrogen atoms has been replaced by tert-butoxycarbonyl.

The term "C$_{1-6}$-alkoxycarbonyl-C$_{1-6}$-alkylaminocarbonyl-C$_{1-6}$-alkoxy" denotes an C$_{1-6}$-alkoxy group wherein one of the hydrogen atoms of the C$_{1-6}$-alkoxy group has been replaced by a C$_{1-6}$-alkoxycarbonyl-C$_{1-6}$-alkylaminocarbonyl group. Particular example is methoxy wherein one of the hydrogen atoms has been replaced by tert-butoxycarbonyl-methylamino.

The term "C$_{1-6}$-alkoxycarbonyl-C$_{1-6}$-alkylaminocarbonyl-C$_{1-6}$-alkyl" denotes an C$_{1-6}$-alkyl group wherein one of the hydrogen atoms of the C$_{1-6}$-alkyl group has been replaced by a C$_{1-6}$-alkoxycarbonyl-C$_{1-6}$-alkylaminocarbonyl group. Particular example is methyl wherein one of the hydrogen atoms has been replaced by tert-butoxycarbonyl-methylaminocarbonyl.

The term "C$_{1-6}$-alkoxycarbonyl-C$_{1-6}$alkylaminocarbonyl" denotes a group of the formula —C(O)—R', wherein R' is a C$_{1-6}$-alkoxycarbonyl-C$_{1-6}$alkylamino group. Particular example is a group wherein R' is tert-butoxycarbonylmethylamino.

The term "C$_{1-6}$-alkoxycarbonyl-C$_{1-6}$-alkylamino" denotes a group of the formula —NH—R', wherein R' is an C$_{1-6}$-alkoxycarbonyl-C$_{1-6}$-alkyl group. Particular example is a group wherein R' is tert-butoxycarbonylmethyl.

The term "C$_{1-6}$-alkoxycarbonyl-C$_{1-6}$-alkyl" denotes an C$_{1-6}$-alkyl group wherein one of the hydrogen atoms of the C$_{1-6}$-alkyl group has been replaced by an C$_{1-6}$-alkoxycarbonyl group. Particular example is a methyl wherein one of the hydrogen atoms of has been replaced by a tert-butoxycarbonyl.

The term "C$_{1-6}$-alkyl" denotes a monovalent linear or branched saturated hydrocarbon group of 1 to 6 carbon atoms. Examples of C$_{1-6}$-alkyl include methyl, ethyl, propyl, isopropyl, n-butyl, iso-butyl, sec-butyl, tert-butyl and pentyl. Particular C$_{1-6}$-alkyl groups are methyl and isopropyl. In the case of R$^2$, particular example is isopropyl.

The term "C$_{1-6}$-alkylsilyloxy" denotes a —O—SiR'R''R''', wherein R', R'' and R''' are independently selected C$_{1-6}$-alkyl groups. Examples of C$_{1-6}$-alkylsilyloxy include groups, wherein R', R'' and R''' are independently selected from methyl, ethyl, propyl, isopropyl, n-butyl, iso-butyl, sec-butyl, tert-butyl and pentyl.

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "aryl(halo)-C$_{1-6}$-alkyl" denotes a halo-C$_{1-6}$-alkyl group wherein one of the hydrogen atoms of the halo-C$_{1-6}$-alkyl group has been replaced by an aryl group. Particular examples are groups wherein the aryl group is phenyl. Further particular example is phenyl-difluoromethyl.

The term "aryl-C$_{1-6}$-alkyl" denotes an —C$_{1-6}$-alkyl group wherein one of the hydrogen atoms of the C$_{1-6}$-alkyl group has been replaced by an aryl group. Particular aryl-C$_{1-6}$-alkyl group is phenyl-C$_{1-6}$-alkyl. Further particular examples of aryl-C$_{1-6}$-alkyl are phenylmethyl and phenylpropyl. Furthermore particular examples of aryl-C$_{1-6}$-alkyl is phenylmethyl.

The term "aryl-C$_{1-6}$-alkoxy" denotes an —C$_{1-6}$-alkoxy group wherein one of the hydrogen atoms of the —C$_{1-6}$-alkoxy group has been replaced by an aryl group. Particular examples are groups wherein the aryl group is phenyl. Particular aryl-C$_{1-6}$-alkoxy group is phenylmethoxy.

The term "aryloxy" denotes a group of the formula —O—R', wherein R' is an aryl group. Particular examples of aryloxy group are groups wherein R' is phenyl.

The term "aryloxy-C$_{1-6}$-alkyl" denotes an C$_{1-6}$-alkyl group wherein one of the hydrogen atoms of the C$_{1-6}$-alkyl group has been replaced by an aryloxy group. Particular examples are groups wherein the aryloxy group is phenoxy. Further particular example of aryloxy-C$_{1-6}$-alkyl is phenoxyalkyl. Further particular example is phenoxymethyl.

The term "aryloxy(halo)-C$_{1-6}$-alkyl" denotes a halo-C$_{1-6}$-alkyl group wherein one of the hydrogen atoms of the halo-$C_{1-6}$-alkyl group has been replaced by an aryloxy group. Particular examples are groups wherein the aryloxy group is phenoxy.

The term "arylcarbonyl" denotes a group of the formula —C(O)—R', wherein R' is an aryl group. Particular example is a group wherein R' is phenyl.

The term "aryl(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by an aryl group. Particular examples are groups wherein the aryl group is phenyl. Further particular example is phenyldifluorocyclopropyl.

The term "aryl-$C_{3-8}$-cycloalkyl" denotes a halo-$C_{3-8}$-cycloalkyl group wherein one of the hydrogen atoms of the $C_{3-8}$-cycloalkyl group has been replaced by an aryl group. Particular examples are groups wherein the aryl group is phenyl. Further particular example is phenylcyclopropyl.

The term "aryloxy-$C_{3-8}$-cycloalkyl" denotes a $C_{3-8}$-cycloalkyl group wherein one of the hydrogen atoms of the $C_{3-8}$-cycloalkyl group has been replaced by an aryloxy group. Particular examples are groups wherein the aryloxy group is phenoxy. Further particular example is phenyldifluorocyclopropyl.

The term "aryloxy(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by an aryloxy group. Particular examples are groups wherein the aryloxy group is phenoxy. Further particular example is phenoxy-difluorocyclopropyl.

The term "aryloxy-$C_{3-8}$-cycloalkyl" denotes a $C_{3-8}$-cycloalkyl group wherein one of the hydrogen atoms of the $C_{3-8}$-cycloalkyl group has been replaced by an aryloxy group. Particular examples are groups wherein the aryloxy group is phenoxy. Further particular example is phenoxy-cyclopropyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "carboxy" denotes a —COOH group.

The term "carboxy-$C_{1-6}$-alkoxy" denotes an $C_{1-6}$-alkoxy group wherein one of the hydrogen atoms of the $C_{1-6}$-alkoxy group has been replaced by a carboxy group. Particular example is carboxymethoxy.

The term "carboxy-$C_{1-6}$-alkyl" denotes an $C_{1-6}$-alkyl group wherein one of the hydrogen atoms of the $C_{1-6}$-alkyl group has been replaced by a carboxy group. Particular example is carboxymethyl.

The term "carboxy-$C_{1-6}$-alkylaminocarbonyl-$C_{1-6}$alkoxy" denotes an $C_{1-6}$-alkoxy group wherein one of the hydrogen atoms of the $C_{1-6}$-alkoxy group has been replaced by a carboxy-$C_{1-6}$-alkylaminocarbonyl group. Particular example is carboxymethylaminocarbonylmethoxy.

The term "carboxy-$C_{1-6}$alkylaminocarbonyl-$C_{1-6}$alkyl" denotes an $C_{1-6}$-alkyl group wherein one of the hydrogen atoms of the $C_{1-6}$-alkyl group has been replaced by a carboxy-$C_{1-6}$alkylaminocarbonyl group. Particular example is carboxymethylaminocarbonylmethyl.

The term "carboxy-$C_{1-6}$alkylaminocarbonyl group" denotes a group of the formula —C(O)—R', wherein R' is a carboxy-$C_{1-6}$alkylamino group. Particular example is carboxymethylamino.

The term "carboxy-$C_{1-6}$alkylamino" denotes a group of the formula —NH—R', wherein R' is a carboxy-$C_{1-6}$alkyl group. Particular example is a group wherein R' is carboxymethyl.

The term "cyano" denotes a —C≡N group.

The term "$C_{3-8}$-cycloalkyl" denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Particular monocyclic cycloalkyl groups are cyclopropyl, cyclobutanyl, cyclopentyl and cyclohexyl. More particular monocyclic cycloalkyl group is cyclopropyl.

The term "$C_{3-8}$-cycloalkyl(halo)-$C_{1-6}$-alkyl" denotes a halo-$C_{1-6}$-alkyl group wherein one of the hydrogen atoms of the halo-$C_{1-6}$-alkyl group has been replaced by an $C_{3-8}$-cycloalkyl group.

The term "$C_{3-8}$-cycloalkyl-$C_{1-6}$-alkyl" denotes an —$C_{1-6}$-alkyl group wherein one of the hydrogen atoms of the $C_{1-6}$-alkyl group has been replaced by an $C_{3-8}$-cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Particular examples of cycloalkylalkyl are cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Further particular examples cycloalkylalkyl is cyclohexylethyl.

The term "halo-$C_{1-6}$-alkoxy" denotes an $C_{1-6}$-alkoxy group wherein at least one of the hydrogen atoms of the $C_{1-6}$-alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups is difluoromethoxy.

The term "halo-$C_{1-6}$-alkyl" denotes an $C_{1-6}$-alkyl group wherein at least one of the hydrogen atoms of the $C_{1-6}$-alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoroethyl.

The term "halo-$C_{3-8}$-cycloalkyl" denotes an $C_{3-8}$-cycloalkyl group wherein at least one of the hydrogen atoms of the $C_{3-8}$-cycloalkyl group has been replaced by the same or different halogen atoms.

The term "halogen" and "halo" are used interchangeably herein and denote fluoro, chloro, bromo or iodo. Particular halogen is chloro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, and benzothiophenyl.

Particular heteroaryl groups are pyrazinyl, pyridinyl, pyrimidinyl and thiophenyl. In the case of substituent $R^{11}$, particular heteroaryl groups are pyrazinyl, pyridinyl, and thiophenyl.

The term "heteroaryl(halo)-$C_{1-6}$-alkyl" denotes a halo-$C_{1-6}$-alkyl group wherein one of the hydrogen atoms of the halo-$C_{1-6}$-alkyl group has been replaced by a heteroaryl group.

The term "heteroaryl-$C_{1-6}$-alkyl" denotes an $C_{1-6}$-alkyl group wherein one of the hydrogen atoms of the $C_{1-6}$-alkyl group has been replaced by a heteroaryl group.

The term "heteroaryl-$C_{1-6}$-alkoxy" denotes an $C_{1-6}$-alkoxy group wherein one of the hydrogen atoms of the $C_{1-6}$-alkoxy group has been replaced by a heteroaryl group.

The term "heteroaryloxy" denotes a group of the formula —O—R', wherein R' is a heteroaryl group.

The term "heteroaryloxy-$C_{1-6}$-alkyl" denotes an $C_{1-6}$-alkyl group wherein one of the hydrogen atoms of the $C_{1-6}$-alkyl group has been replaced by a heteroaryloxy group.

The term "heteroaryloxy(halo)-$C_{1-6}$-alkyl" denotes a halo-$C_{1-6}$-alkyl group wherein one of the hydrogen atoms of the halo-$C_{1-6}$-alkyl group has been replaced by a heteroaryloxy group.

The term "heteroarylcarbonyl" denotes a group of the formula —C(O)—R', wherein R' is a heteroaryl group. Particular heteroarylcarrbonyl is a group wherein R' is pyridinyl.

The term "heteroaryl(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heteroaryl group.

The term "heteroaryl-$C_{3-8}$-cycloalkyl" denotes a halo-$C_{3-8}$-cycloalkyl group wherein one of the hydrogen atoms of the $C_{3-8}$-cycloalkyl group has been replaced by a heteroaryl group.

The term "heteroaryloxy-$C_{3-8}$-cycloalkyl" denotes a $C_{3-8}$-cycloalkyl group wherein one of the hydrogen atoms of the $C_{3-8}$-cycloalkyl group has been replaced by a heteroaryloxy group.

The term "heteroaryloxy(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heteroaryloxy group.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydrooxazolyl, tetrahydro-pyridinyl, or dihydropyranyl.

The term "heterocycloalkyl-$C_{1-6}$-alkyl" denotes an $C_{1-6}$-alkyl group wherein one of the hydrogen atoms of the $C_{1-6}$-alkyl group has been replaced by a heterocycloalkyl group.

The term "heterocycloalkyl-$C_{1-6}$-alkoxy" denotes an $C_{1-6}$-alkoxy group wherein one of the hydrogen atoms of the $C_{1-6}$-alkoxy group has been replaced by a heterocycloalkyl group.

The term "heterocycloalkyl(halo)-$C_{1-6}$-alkyl" denotes a halo-$C_{1-6}$-alkyl group wherein one of the hydrogen atoms of the halo-$C_{1-6}$-alkyl group has been replaced by a heterocycloalkyl group.

The term "heterocycloalkyl(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heterocycloalkyl group.

The term "hydroxy" denotes a —OH group.

The term "oxo" denotes a =O group.

The term "phenoxy" denotes a group of the formula —O—R', wherein R' is a phenyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point.

Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

$R^9$ is selected from
i) H, and
ii) hydroxy,
iii) $C_{1-6}$-alkoxy,
iv) phenyl substituted with $R^{15}$, $R^{16}$ and $R^{17}$, and
v) $C_{1-6}$-alkylsilyloxy;

$R^{11}$ is selected from
i) phenyl substituted with $R^{18}$, $R^{19}$ and $R^{20}$,
ii) phenyl-$C_{3-8}$-cycloalkyl substituted with $R^{18}$, $R^{19}$ and $R^{20}$,
iii) phenyl(halo)-$C_{1-6}$-alkyl substituted with $R^{18}$, $R^{19}$ and $R^{20}$, and
iv) heteroaryl substituted with $R^{18}$, $R^{19}$ and $R^{20}$, wherein heteroaryl is selected from
   a. pyrazinyl,
   b. pyridinyl, and
   c. thiophenyl;

$R^{12}$ is selected from
i) H, and
ii) $C_{1-6}$-alkoxy, $R^{15}$ is selected from
i) H,
ii) halogen, and

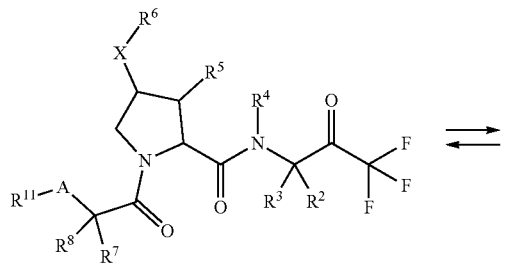

Depending on the individual compound and the conditions it has been exposed, the $CF_3$-ketone moiety in compounds I exist in part, mainly or totally in form of its hydrate. Thus, any description of a $CF_3$-ketone moiety always describes both ketone and hydrate form.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Another embodiment of the present invention are compounds according to formula (I) as described herein, wherein
$R^2$ is $C_{1-6}$-alkyl;
$R^3$, $R^4$, $R^5$ and $R^7$ are H;
X is selected from
 i) —O—,
 ii) —S—, and
 iii) —S(O)$_2$—;
$R^6$ is phenyl-$C_{1-6}$-alkyl substituted with $R^{12}$, $R^{13}$ and $R^{14}$;
A is selected from
 i) —O—,
 ii) —CH$_2$—,
 iii) —S(O)$_2$NR$^{10}$— and
 iv) —C(O)NR$^{10}$—;
$R^8$ is selected from
 i) H, and
 ii) —CH$_2$R$^9$;

iii) amino-$C_{1-6}$-alkyl substituted on the nitrogen atom by one H and one $C_{1-6}$-alkoxycarbonyl;

$R^{18}$ is selected from
i) H,
ii) halogen, and
iii) halo-$C_{1-6}$-alkyl;

$R^{13}$, $R^{14}$, $R^{16}$, $R^{17}$, $R^{19}$ and $R^{20}$ are H;

or pharmaceutically acceptable salts;

with the proviso that N-[(1S)-1-[[(1S)-1-[(2S,4R)-4-benzyloxy-2-[(1-ethyl-3,3,3-trifluoro-2-oxo-propyl)carbamoyl]pyrrolidine-1-carbonyl]-2-methyl-propyl]carbamoyl]-2-methyl-propyl]pyrazine-2-carboxamide is excluded.

Another particular embodiment of the present invention are compounds according to formula (I) as described herein, wherein $R^2$ is $C_{1-6}$-alkyl.

Another particular embodiment of the present invention are compounds according to formula (I) as described herein, wherein $R^3$, $R^4$, $R^5$ and $R^7$ are H.

Another particular embodiment of the present invention are compounds according to formula (I) as described herein, wherein X is selected from
i) —O—, and
ii) —S(O)$_2$—.

A further particular embodiment of the present invention are compounds according to formula (I) as described herein, wherein X is —O—.

Another particular embodiment of the present invention are compounds according to formula (I) as described herein, wherein $R^6$ is phenyl-$C_{1-6}$-alkyl substituted with $R^{12}$, $R^{13}$ and $R^{14}$.

A particular embodiment of the present invention are compounds according to formula (I) as described herein, wherein A is selected from
i) —O—, and
ii) —CH$_2$—.

A further particular embodiment of the present invention are compounds according to formula (I) as described herein, wherein A is —O—.

A particular embodiment of the present invention are compounds according to formula (I) as described herein, wherein R$^8$ is H.

A particular embodiment of the present invention are compounds according to formula (I) as described herein, wherein R$^9$ is selected from
i) H, and
ii) hydroxy,
iii) C$_{1-6}$-alkoxy,
iv) phenyl substituted with R$^{15}$, R$^{16}$ and R$^{17}$, and
v) C$_{1-6}$-alkylsilyloxy.

A further particular embodiment of the present invention are compounds according to formula (I) as described herein, wherein R$^9$ is phenyl substituted with R$^{15}$, R$^{16}$ and R$^{17}$.

A particular embodiment of the present invention are compounds according to formula (I) as described herein, wherein R$^{11}$ is selected from
i) phenyl substituted with R$^{18}$, R$^{19}$ and R$^{20}$,
ii) phenyl-C$_{3-8}$-cycloalkyl substituted with R$^{18}$, R$^{19}$ and R$^{20}$,
iii) phenyl(halo)-C$_{1-6}$-alkyl substituted with R$^{18}$, R$^{19}$ and R$^{20}$, and
iv) heteroaryl substituted with R$^{18}$, R$^{19}$ and R$^{20}$, wherein heteroaryl is selected from
a. pyrazinyl,
b. pyridinyl, and
c. thiophenyl.

A further particular embodiment of the present invention are compounds according to formula (I) as described herein, wherein R$^{11}$ is phenyl substituted with R$^{18}$, R$^{19}$ and R$^{20}$.

A particular embodiment of the present invention are compounds according to formula (I) as described herein, wherein R$^{12}$ is selected from
i) H, and
ii) C$_{1-6}$-alkoxy.

A further particular embodiment of the present invention are compounds according to formula (I) as described herein, wherein R$^{12}$ is H.

A particular embodiment of the present invention are compounds according to formula (I) as described herein, wherein R$^{15}$ is selected from
i) H,
ii) halogen, and
iii) amino-C$_{1-6}$-alkyl substituted on the nitrogen atom by one H and one C$_{1-6}$-alkoxycarbonyl.

A further particular embodiment of the present invention are compounds according to formula (I) as described herein, wherein R$^{15}$ is H.

A particular embodiment of the present invention are compounds according to formula (I) as described herein, wherein R$^{18}$ is selected from
i) H,
ii) halogen, and
iii) halo-C$_{1-6}$-alkyl.

A further particular embodiment of the present invention are compounds according to formula (I) as described herein, wherein R$^{18}$ is halogen.

A particular embodiment of the present invention are compounds according to formula (I) as described herein, wherein R$^{13}$, R$^{14}$, R$^{16}$, R$^{17}$, R$^{19}$ and R$^{20}$ are H.

A furthermore particular embodiment of the present invention are compounds according to formula (I) as described herein, wherein
R$^2$ is C$_{1-6}$-alkyl;
R$^3$, R$^4$, R$^5$ and R$^7$ are H;
X is —O—;
R$^6$ is phenyl-C$_{1-6}$-alkyl substituted with R$^{12}$, R$^{13}$ and R$^{14}$;
A is —O—;
R$^8$ is H;
R$^9$ is R$^9$ is phenyl substituted with R$^{15}$, R$^{16}$ and R$^{17}$;
R$^{11}$ is phenyl substituted with R$^{18}$, R$^{19}$ and R$^{20}$;
R$^{12}$, R$^{13}$, R$^{14}$, R$^{15}$, R$^{16}$, R$^{17}$, R$^{19}$ and R$^{20}$ are H.
R$^{18}$ is halogen;
or pharmaceutically acceptable salts;

Particular examples of compounds of formula (I) as described herein are selected from
N—((S)-3-(3-chlorophenyl)-1-((2S,4R)-4-((4-methoxybenzyl)sulfonyl)-2-(((S)-1,1,1-trifluoro-4-methyl-2-oxopentan-3-yl)carbamoyl)pyrrolidin-1-yl)-1-oxopropan-2-yl) picolinamide;
N—((S)-3-(3-chlorophenyl)-1-((2S,4R)-4-((4-methoxybenzyl)sulfonyl)-2-(((S)-1,1,1-trifluoro-4-methyl-2-oxopentan-3-yl)carbamoyl)pyrrolidin-1-yl)-1-oxopropan-2-yl) pyrazine-2-carboxamide;
(2S,4R)-1-[(2S)-2-[[2-(3-chlorophenyl)-2,2-difluoroacetyl]amino]propanoyl]-4-[(4-methoxyphenyl)methylsulfonyl]-N-[(3S)-1,1,1-trifluoro-4-methyl-2-oxopentan-3-yl]pyrrolidine-2-carboxamide;
(2S,4R)-1-[(2S)-2-[[2,2-difluoro-2-[2-(trifluoromethyl)phenyl]acetyl]amino]propanoyl]-4-[(4-methoxyphenyl)methylsulfonyl]-N-[(3S)-1,1,1-trifluoro-4-methyl-2-oxopentan-3-yl]pyrrolidine-2-carboxamide;
(2S,4R)-1-[(2S)-2-[[2-(3-chlorophenyl)-2,2-difluoroacetyl]amino]-3-methoxypropanoyl]-4-[(4-methoxyphenyl)methylsulfonyl]-N-[(3S)-1,1,1-trifluoro-4-methyl-2-oxopentan-3-yl]pyrrolidine-2-carboxamide;
(2S,4R)-1-[(2S)-2-[[2,2-difluoro-2-[2-(trifluoromethyl)phenyl]acetyl]amino]-3-methoxypropanoyl]-4-[(4-methoxyphenyl)methylsulfonyl]-N-[(3S)-1,1,1-trifluoro-4-methyl-2-oxopentan-3-yl]pyrrolidine-2-carboxamide;
tert-butyl N-[[4-[(2S)-2-[[2-(3-chlorophenyl)-2,2-difluoroacetyl]amino]-3-[(2S,4R)-4-[(4-methoxyphenyl)methylsulfonyl]-2-[[(3S)-1,1,1-trifluoro-4-methyl-2-oxopentan-3-yl]carbamoyl]pyrrolidin-1-yl]-3-oxopropyl]phenyl]methyl]carbamate;
tert-butyl N-[[4-[(2S)-2-[(3-chlorobenzoyl)amino]-3-[(2S,4R)-4-[(4-methoxyphenyl)methylsulfonyl]-2-[[(3S)-1,1,1-trifluoro-4-methyl-2-oxopentan-3-yl]carbamoyl]pyrrolidin-1-yl]-3-oxopropyl]phenyl]methyl]carbamate;
tert-butyl N-[[4-[(2S)-2-[[2,2-difluoro-2-[2-(trifluoromethyl)phenyl]acetyl]amino]-3-[(2S,4R)-4-[(4-methoxyphenyl)methylsulfonyl]-2-[[(3S)-1,1,1-trifluoro-4-methyl-2-oxopentan-3-yl]carbamoyl]pyrrolidin-1l-yl]-3-oxopropyl]phenyl]methyl]carbamate;
tert-butyl N-[[4-[(2S)-2-[[1-(4-chlorophenyl)cyclopentanecarbonyl]amino]-3-[(2S,4R)-4-[(4-methoxyphenyl)methylsulfonyl]-2-[[(3S)-1,1,1-trifluoro-4-methyl-2-oxopentan-3-yl]carbamoyl]pyrrolidin-1-yl]-3-oxopropyl]phenyl]methyl]carbamate;
(2S,4R)-1-(2-(3,5-dichlorophenoxy)acetyl)-4-((4-methoxybenzyl)sulfonyl)-N—((S)-1,1,1-trifluoro-4-methyl-2-oxopentan-3-yl)pyrrolidine-2-carboxamide;

(2S,4R)-1-(2-(3,5-dichlorophenoxy)acetyl)-4-((4-methoxy-benzyl)thio)-N-((R)-1,1,1-trifluoro-4-methyl-2-oxopentan-3-yl)pyrrolidine-2-carboxamide;

(2S,4R)-4-(benzyloxy)-1-(3-(3,4-dichlorophenyl)propanoyl)-N—((S)-1,1,1-trifluoro-4-methyl-2-oxopentan-3-yl)pyrrolidine-2-carboxamide;

(2S,4R)-4-(benzyloxy)-1-(2-(3,5-dichlorophenoxy)acetyl)-N—((S)-1,1,1-trifluoro-4-methyl-2-oxopentan-3-yl)pyrrolidine-2-carboxamide;

N—((S)-1-((2S,4R)-4-(benzyloxy)-2-(((S)-1,1,1-trifluoro-4-methyl-2-oxopentan-3-yl)carbamoyl)pyrrolidin-1-yl)-3-(3-chlorophenyl)-1-oxopropan-2-yl)picolinamide;

N—((S)-1-((2S,4R)-4-(benzyloxy)-2-(((S)-1,1,1-trifluoro-4-methyl-2-oxopentan-3-yl)carbamoyl)pyrrolidin-1-yl)-3-(3-chlorophenyl)-1-oxopropan-2-yl)pyrazine-2-carboxamide;

(2S,4R)-4-(benzyloxy)-1-((R)-2-(3,5-dichlorophenoxy)-3-phenylpropanoyl)-N—((S)-1,1,1-trifluoro-4-methyl-2-oxopentan-3-yl)pyrrolidine-2-carboxamide;

(2S,4R)-1-[(2S)-2-[(5-chlorothiophen-2-yl)sulfonylamino]-3-methoxypropanoyl]-4-[(4-methoxyphenyl)methylsulfonyl]-N-[(3S)-1,1,1-trifluoro-4-methyl-2-oxopentan-3-yl]pyrrolidine-2-carboxamide;

(2S,4R)-1-[(2S)-2-[[2-(3-chlorophenyl)-2,2-difluoroacetyl]amino]-3-hydroxypropanoyl]-4-[(4-methoxyphenyl)methylsulfonyl]-N-[(3S)-1,1,1-trifluoro-4-methyl-2-oxopentan-3-yl]pyrrolidine-2-carboxamide;

(2S,4R)-1-[(2S)-3-[4-(aminomethyl)phenyl]-2-[[2-(3-chlorophenyl)-2,2-difluoroacetyl]amino]propanoyl]-4-[(4-methoxyphenyl)methylsulfonyl]-N-[(3S)-1,1,1-trifluoro-4-methyl-2-oxopentan-3-yl]pyrrolidine-2-carboxamide; 2,2,2-trifluoroacetic acid;

(2S,4R)-1-[(2S)-3-[4-(aminomethyl)phenyl]-2-[(3-chlorobenzoyl)amino]propanoyl]-4-[(4-methoxyphenyl)methylsulfonyl]-N-[(3S)-1,1,1-trifluoro-4-methyl-2-oxopentan-3-yl]pyrrolidine-2-carboxamide; 2,2,2-trifluoroacetic acid;

(2S,4R)-1-[(2S)-3-[4-(aminomethyl)phenyl]-2-[[2,2-difluoro-2-[2-(trifluoromethyl)phenyl]acetyl]amino]propanoyl]-4-[(4-methoxyphenyl)methylsulfonyl]-N-[(3S)-1,1,1-trifluoro-4-methyl-2-oxopentan-3-yl]pyrrolidine-2-carboxamide; 2,2,2-trifluoroacetic acid;

(2S,4R)-1-[(2S)-3-[4-(aminomethyl)phenyl]-2-[[1-(4-chlorophenyl)cyclopentanecarbonyl]amino]propanoyl]-4-[(4-methoxyphenyl)methylsulfonyl]-N-[(3S)-1,1,1-trifluoro-4-methyl-2-oxopentan-3-yl]pyrrolidine-2-carboxamide; 2,2,2-trifluoroacetic acid;

and pharmaceutically acceptable salts thereof.

Further particular examples of compounds of formula (I) as described herein are selected from (2S,4R)-1-(2-(3,5-dichlorophenoxy)acetyl)-4-((4-methoxy-benzyl)sulfonyl)-N—((S)-1,1,1-trifluoro-4-methyl-2-oxopentan-3-yl)pyrrolidine-2-carboxamide;

(2S,4R)-4-(benzyloxy)-1-(3-(3,4-dichlorophenyl)propanoyl)-N—((S)-1,1,1-trifluoro-4-methyl-2-oxopentan-3-yl)pyrrolidine-2-carboxamide;

(2S,4R)-4-(benzyloxy)-1-(2-(3,5-dichlorophenoxy)acetyl)-N—((S)-1,1,1-trifluoro-4-methyl-2-oxopentan-3-yl)pyrrolidine-2-carboxamide;

(2S,4R)-4-(benzyloxy)-1-((R)-2-(3,5-dichlorophenoxy)-3-phenylpropanoyl)-N—((S)-1,1,1-trifluoro-4-methyl-2-oxopentan-3-yl)pyrrolidine-2-carboxamide;

and pharmaceutically acceptable salts thereof.

Processes for the manufacture of compounds of formula (I) as described herein are an object of the invention.

Synthesis

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

AcOH=acetic acid, Boc=t-butyloxycarbonyl, BuLi=butyllithium, CDI=1,1-carbonyldiimidazole, Cbz=carboxybenzyl, CSA=camphorsulfonic acid, DCM=dichloromethane, DBU=2,3,4,6,7,8,9,10-octahydro-pyrimido[1,2-a]azepine, DCE=1,2-dichloroethane, DIAD=diisopropylazodicarboxylate, DIBALH=di-i-butylaluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, $Et_2O$=diethylether, $Et_3N$=triethylamine, eq=equivalents, Fmoc=fluorenylmethoxycarbonyl, HATU=O-(7-azabenzotriazol-1-yl)-1,1,3,3-tetramethyluronium hexafluorophosphate, HPLC=high performance liquid chromatography, HOBt=1-hydroxybenzo-triazole, Huenig's base=$iPr_2NEt$=N-ethyl diisopropylamine, IPA=isopropyl alcohol, IPC=in process control, LAH=lithium aluminium hydride, LDA=lithium diisopropylamide, $LiBH_4$=lithium borohydride, MeOH=methanol, $NaBH_3CN$, sodium cyanoborohydride, $NaBH_4$=sodium borohydride, NaI=sodium iodide, PG=protecting group, Red-Al=sodium bis(2-methoxyethoxy) aluminium hydride, RT=room temperature, TBDMSCl=t-butyldimethylsilyl chloride, TBTU=O-benzotriazol-1-yl-N,N,N',N'-tetramethyl-uronium tetrafluoroborate, TFA=trifluoroacetic acid, THF=tetrahydrofuran, quant=quantitative.

Compounds of formula (I) wherein A is $S(O)_2NR^{10}$ or $C(O)NR^{10}$ can be produced as outlined in scheme 1. Amide coupling of N-protected-4-substituted-pyrrolidine-2-carboxylic acid 1 (scheme 1), such as (2S,4R)-4-[(4-methoxyphenyl)methylsulfonyl]-1-[(2-methylpropan-2-yl)oxycarbonyl]pyrrolidine-2-carboxylic acid with trifluoromethyl compounds 2 can be accomplished by using one of the well-known coupling reagents such as TBTU, HATU, EDCI/HOBt, etc. and a base like Huenig's base or triethyl amine in a solvent like N,N-dimethylformamide preferably between 0° C. and room temperature to give compounds 3 (step a). Subsequent deprotection under appropriate conditions, depending on the nature of the protecting group PG (step b), gives compounds 4 (e.g. acidic conditions such as treatment with 4M HCl in dioxane in a solvent like MeOH or treatment with TFA in DCM around room temperature can be used for removal of a Boc protecting group, catalytic hydrogenation conditions using suitable catalysts such as Pd/C, Pd(OH)$_2$ in a solvent like MeOH, EtOH or AcOEt around room temperature can be used for removal of a Cbz protecting group, etc.). Reaction of compounds 4 with a N-protected-α-amino acid compounds 5, such as (2S)-2-(tert-butoxycarbonylamino)-3-(3-chlorophenyl)propanoic acid, can be performed by using one of various coupling reagents such as TBTU, HATU, EDCI/HOBt, etc., and a base like Huenig's base or triethyl amine in a solvent like N,N-dimethylformamide preferably between 0° C. and room temperature to give compounds 6 (step c). Subsequent deprotection under appropriate conditions, depending on the nature of the protecting group PG' (step d), gives compounds 7 (e.g. acidic conditions such as treatment with 4M HCl in dioxane in a solvent like MeOH or treatment with TFA in DCM around room temperature can be used for removal of a Boc protecting group, catalytic hydrogenation conditions using suitable catalysts such as Pd/C, Pd(OH)$_2$ in a solvent like MeOH, EtOH or AcOEt around room temperature can be used for removal of a Cbz protecting group, treatment with a mild base such as piperidine in a solvent like DCM around room temperature can be used for removal of a Fmoc protecting group, etc.). Reaction of compounds 7 with the appropriate carboxylic acid compounds 8, activated by one of the various coupling reagents such as TBTU, HATU, EDCI/HOBt, etc., and a base like Huenig's base or triethyl amine in a solvent like N,N-dimethylformamide preferably between 0° C. and room temperature gives compounds 9 (step e). Alternatively, compounds 7 can be reacted with suitable sulfonyl chloride 8' in presence of a base such as Huenig's base or triethyl amine in a solvent like DCM or DMF preferably between 0° C. and room temperature to generate compounds 9 (step e). Oxidation of compounds 9 can e.g. be performed using Swern's conditions (oxalyl chloride, dimethyl sulfoxide, triethyl amine in dichloromethane between −78° C. and RT) or with the help of an appropriate specific oxidizing agent as Dess-Martin Periodinane in a solvent like DCM between 0° C. and room temperature and gives the final products I (step f).

Compounds I containing a tert-butyl-dimethyl-silyloxy or a tert-butoxycarbonylamino moiety in $R^8$, $R^{10}$ or $R^{11}$ can be converted into the corresponding alcohols or amines under appropriate conditions depending on the nature of the functional groups, resulting in modified final compounds I (step g), (e.g. acidic conditions such as treatment with 4M HCl in dioxane or THF can be used for removal of tert-butyl-dimethyl-silyloxy groups and treatment with TFA in DCM around room temperature can be used for removal tert-butoxycarbonylamino groups).

Scheme 1

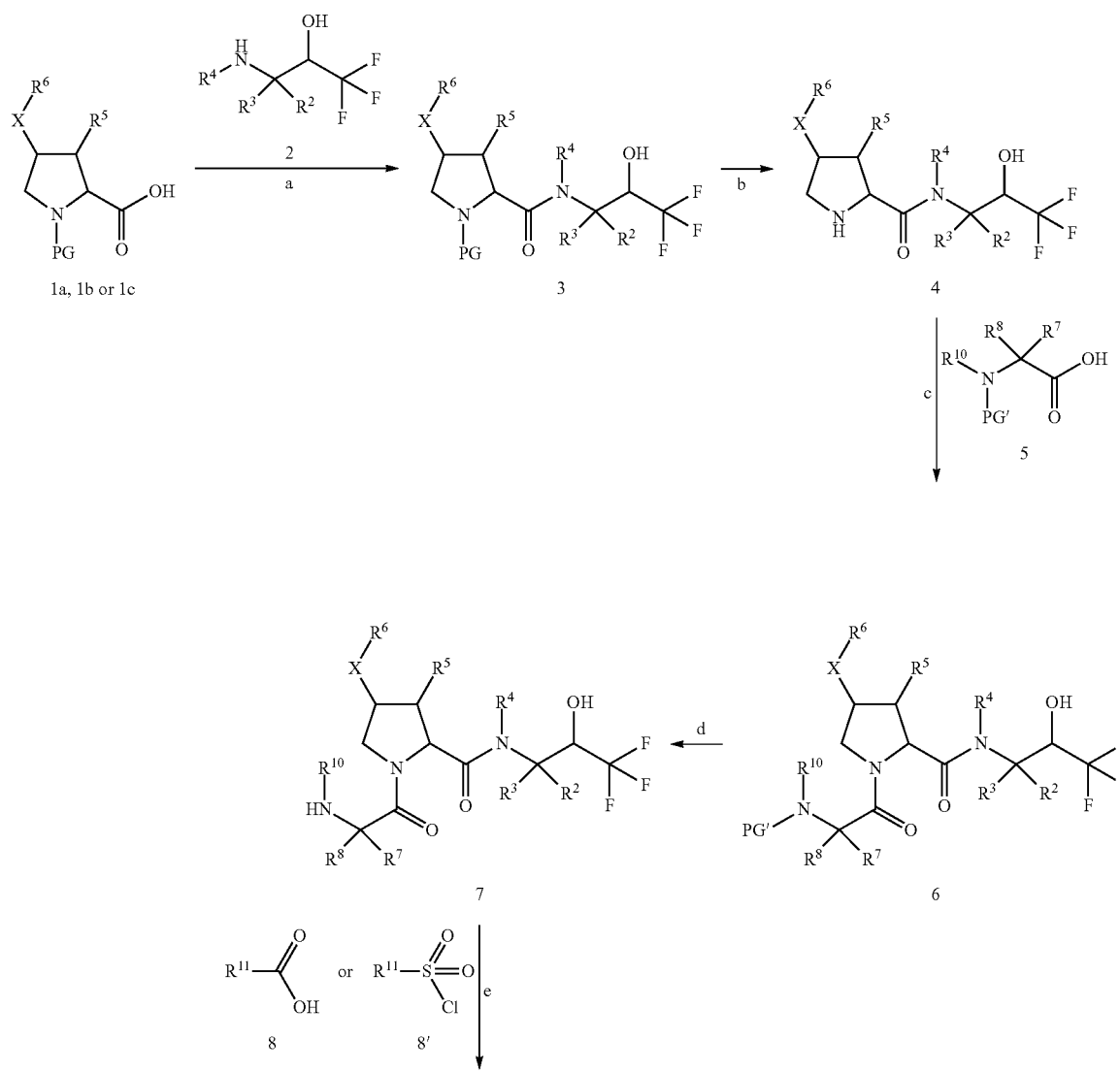

-continued

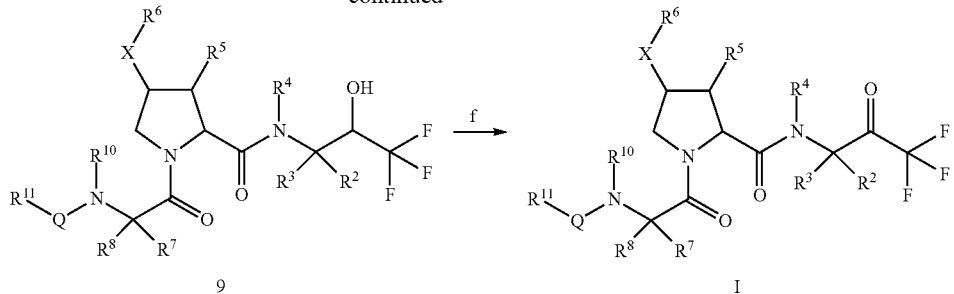

PG is e.g. Boc, Cbz,
PG' is e.g. Boc, Cbz, Fmoc
Q is CO or SO$_2$
X is O, S or SO$_2$

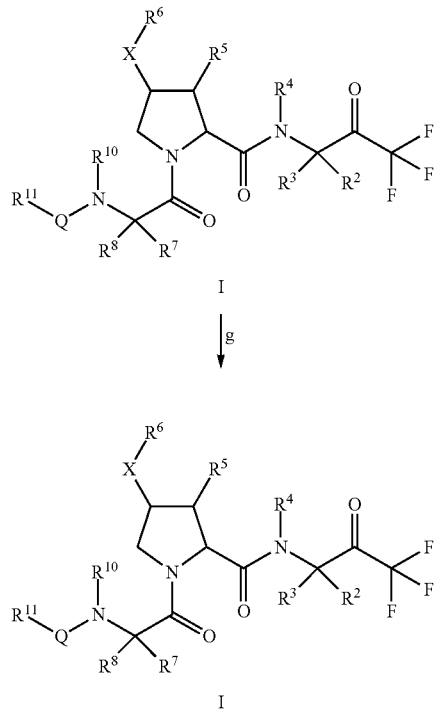

-continued

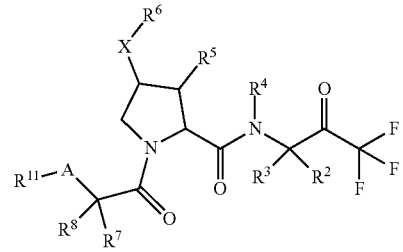

A is C, O CONR$_{10}$ or SO$_2$NR$_{10}$
X is O, S or SO$_2$

In another synthetic variant, as outlined in scheme 2, intermediate 4 of scheme 1 is reacted with a carboxylic acids 5' (for its synthesis, see below in scheme 9 or 10), such as (2R)-3-(3-chlorophenyl)-2-(3,5-dichlorophenoxy)propanoic acid under standard peptide coupling conditions by treatment with a coupling reagent such as TBTU, HATU, EDCI/HOBT, etc., and a base like Huenig's base or TEA in an inert solvent like N,N-dimethylformamide to yield 6' (step a). Oxidation of the free alcohol, e.g., with Dess Martin periodinane, in an inert solvent like DCM, delivers finally the target molecule I (step b).

Scheme 2

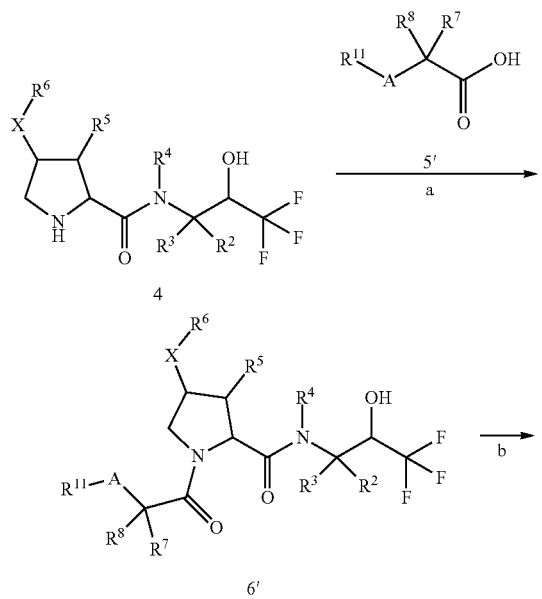

N-protected-4-substituted-pyrrolidines 1 bearing a benzylsulfonyl or a benzylsulfanyl substituent can be prepared by methods known in the art or as described in the general synthetic procedure below (scheme 3). Commercially available (2S,4S)—N-protected-4-substituted-pyrrolidine-1,2-dicarboxylate 31 are treated with e.g. phenylmethanethiol or (4-methoxyphenyl)methanethiol and potassium tert-butoxide in DMF (for Cl: preferably between −5° C. and room temperature; for Br: 0° C. to room temperature; for Mesylate or Tosylate: room temperature to 100° C.) to give compounds 32 with inversion of the configuration (step a). Subsequent sulfide oxidation using mCPBA in a solvent like DCM preferably between 0° C. and room temperature give compounds 33 (step b). Hydrolysis of esters 32 or 33 can be achieved preferably with aqueous lithium hydroxide in a solvent like THF, MeOH or a mixture of THF/MeOH at 0° C. or sodium hydroxide in a solvent like ethanol between 0° C. and room temperature to give acids 1a and 1b (step c).

Scheme 3

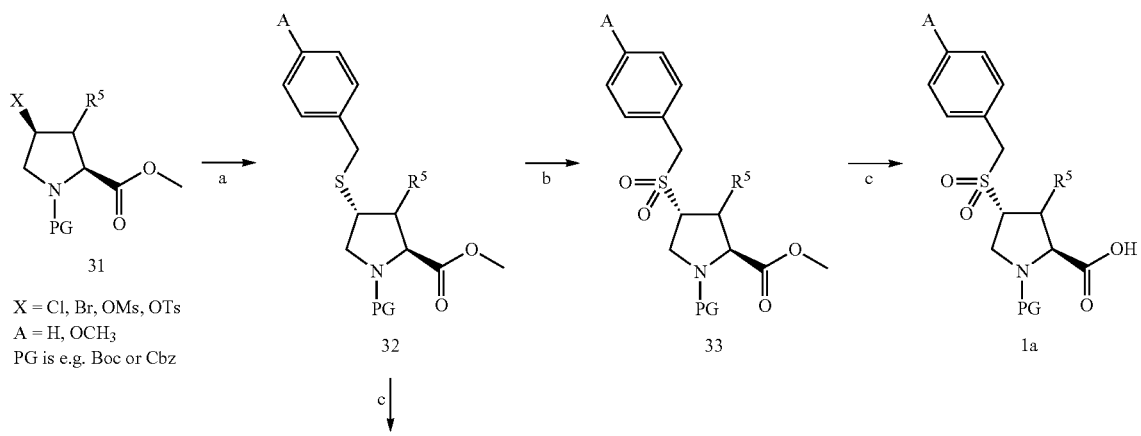

N-protected-4-substituted-pyrrolidines 1 can be prepared by methods known in the art or as described in the general synthetic procedure below (scheme 4). Compounds 1 bearing a benzyloxy substituent can be reacted with commercially available (2S,4S)—N-protected-4-hydroxypyrrolidine-1,2-dicarboxylate 41 using benzylbromide in a solvent like DMF in the presence of a base such as NaH preferably between 0° C. and room temperature to give compounds 42 with inversion of the configuration (step a). Alternatively, compounds 1 bearing a 4-methoxybenzyloxy substituent can be reacted with commercially available (2S,4R)-4-hydroxypyrrolidine-1,2-dicarboxylate 43 with suitable carboxylic acids 5' (for its synthesis, see below in scheme 9 or 10) under standard coupling conditions by using a coupling reagent such as HATU and a base like Huenig's base in a solvent like DMF preferably between 0° C. and room temperature to give compounds 44 with retention of the configuration (step a'). Subsequent reaction of (2S,4R)—N-protected-4-hydroxypyrrolidine-1,2-dicarboxylate 44 (PG=R$^{11}$ACR$^7$R$^8$CO) with 4-methoxybenzyl 2,2,2-trichloroacetimidate in a solvent like DCM or DCE in the presence of a catalytic amount of acid such as p-toluenesulfonic acid or trifluoromethanesulfonic acid preferably between 0° C. and room temperature to give compounds 42 (PG=R$^{11}$ACR$^7$R$^8$CO; step b). Hydrolysis of esters 42 can be achieved preferably with aqueous lithium hydroxide in a solvent like THF, MeOH or a mixture of THF/MeOH at 0° C. or sodium hydroxide in a solvent like MeOH or ethanol between 0° C. and room temperature to give acids 1c (step c).

Scheme 4

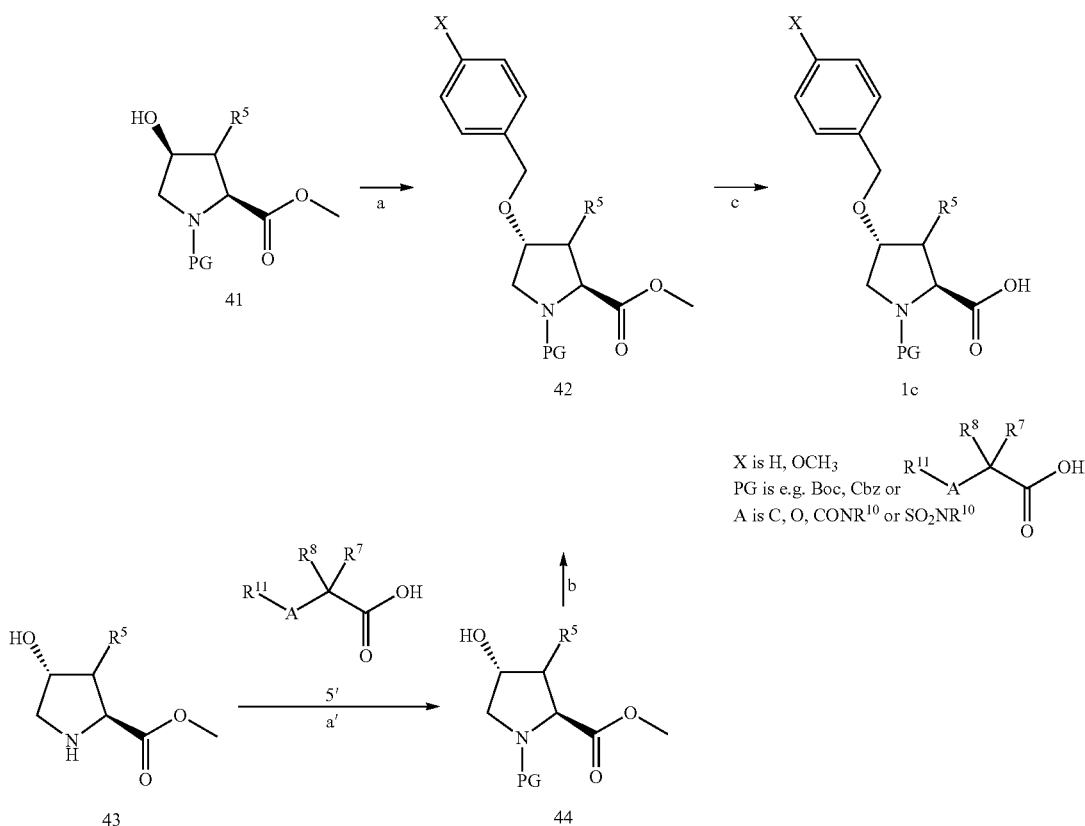

Compounds 2 can be prepared by a variety of conditions, which may be exemplified by the general synthetic procedure below (scheme 5). Known N-protected-oxazolidin-5-one derivatives 52, preferably with fully defined stereochemistry, can be prepared by formylation of the corresponding enantiopure N-protected-α-amino acid derivatives 51, such as Cbz-L-valine, with paraformaldehyde in presence of Lewis acid catalysts, such as $ZnCl_2$, $AlCl_3$, $BF_3$ or preferably in presence of Brönsted acid catalysts, such as pTsOH, CSA, AcOH, $H_2SO_4$, in a solvent like toluene, and in a temperature range preferably between 75° C. and about 90° C. (step a). Subsequent nucleophilic addition of a trifluoromethylating reagent, such as trifluoromethyltrimethylsilane (Ruppert's reagent), in the presence of a catalytic amount of a fluoride source such as TBAF or CsF, in a solvent like THF, and in a temperature range preferably between 0° C. and about 10° C., followed by deprotection of the TMS group by treatment in MeOH, gives compounds 53 with preferred stereochemistry as shown if $R^3$=H (step b). Stereoselective reduction of compounds 53 using suitable reducing agents such as $NaBH_4$, $LiBH_4$, $LiBHEt_3$, DIBALH, $NaBH_4$—$CeCl_3$ preferably $NaBH_4$—$ZnCl_2$, in a solvent like MeOH, EtOH, IPA, tBuOH, THF, DMF, preferably in tert-butyl methyl ether around room temperature, followed by alkaline hydrolysis with a base, such as aqueous or non aqueous sodium, potassium or cesium carbonate, sodium or potassium hydroxide, in a solvent like MeOH, EtOH and water around room temperature, gives compounds 54 (step c). Finally, deprotection under appropriate conditions, depending on the nature of the protecting group PG (step d), gives compounds 55 (e.g. acidic conditions such as treatment with 4M HCl in dioxane in a solvent like MeOH or treatment with TFA in DCM around room temperature can be used for removal of a Boc protecting group, catalytic hydrogenation conditions using suitable catalysts such as Pd/C, $Pd(OH)_2$ in a solvent like MeOH, EtOH or AcOEt around room temperature can be used for removal of a Cbz protecting group, treatment with a mild base such as piperidine in a solvent like DCM around room temperature can be used for removal of a Fmoc protecting group). Alternatively, the hydroxy function of N-protected-α-amino trifluoromethyl alcohol derivatives 54 can be protected with a suitable protecting group, such as MOM, MEM, PMB or preferably THP using the appropriate conditions known by the person skilled in the art to give compounds 56 (step e). Subsequent N-alkylation by treatment of compounds 56 with an appropriate base, such as NaH, KH, NaHMDS, LiHMDS, LDA, in a solvent like THF, dioxane, DMF, in a temperature range between −78° C. and 0° C., followed by addition of alkyl or cycloalkyl halides, such as MeI, EtI, iPrI, CyPrI, etc., gives compounds 57 (step f). Finally, removal of both protecting groups PG and PG' under appropriate conditions, depending on the nature of the protecting group (step g), gives compounds 2 (e.g. acidic conditions such as treatment with 4M HCl in dioxane in a solvent like MeOH around room temperature can be used for removal of Boc, MOM, MEM or THP protecting groups, catalytic hydrogenation conditions using suitable catalysts such as Pd/C, $Pd(OH)_2$ in a solvent like MeOH, EtOH or AcOEt around room temperature can be used for removal of Cbz or PMB protecting groups).

Scheme 5

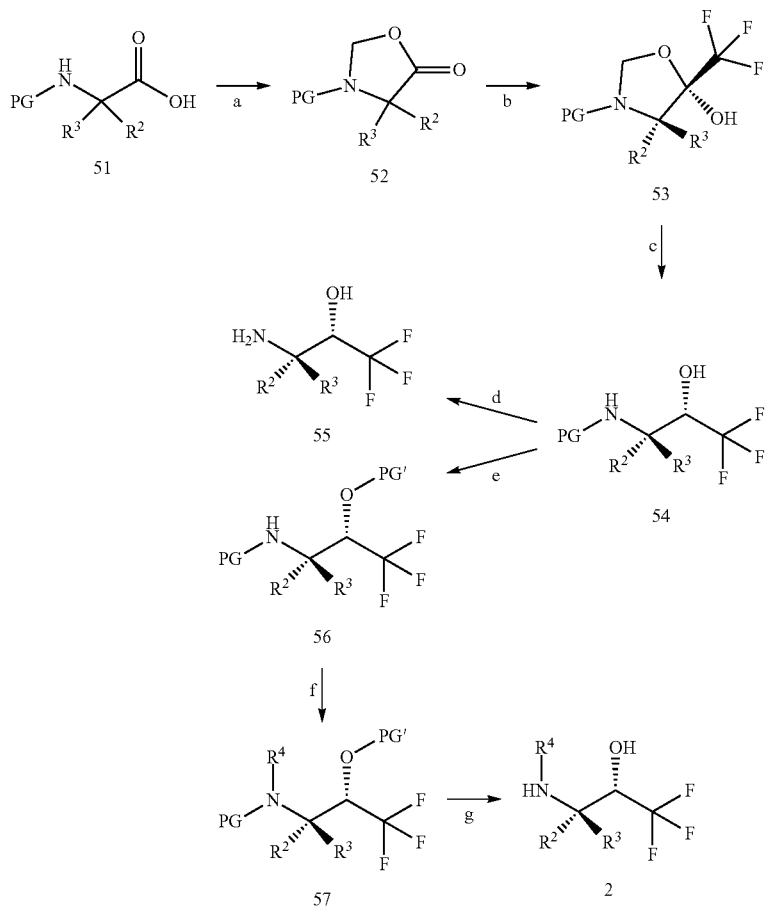

PG is e.g. Boc, Cbz, Fmoc
PG' is e.g. MOM, MEM, Cbz, THP

Carboxylic acids 5' in scheme 2 and 4, can be, if not commercial available, prepared as follows (scheme 9). The appropriate, commercially available alpha-hydroxy substituted propanoate derivative 100 is reacted under typical Mitsunobu conditions using a suitable phenol derivative 101, such as 3,5-dichlorophenol, using e.g. DIAD, triphenylphosphine, in a solvent like THF and in a temperature range between 0° C. and room temperature gives ether derivatives 102 (step a). Alkaline hydrolysis of the ester functional group with an appropriate base, such as aqueous or non aqueous sodium, potassium or cesium carbonate, sodium or potassium hydroxide, preferably aqueous lithium hydroxide, in a solvent like MeOH, EtOH, THF, dioxane, preferably in a mixture of THF/MeOH and in a temperature range between room temperature and the reflux temperature of the solvents, gives the alpha-phenoxy substituted propanoic acid derivative 5' (step b).

Scheme 9

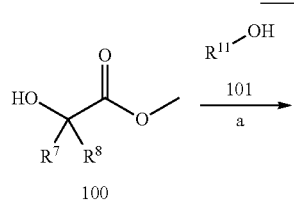

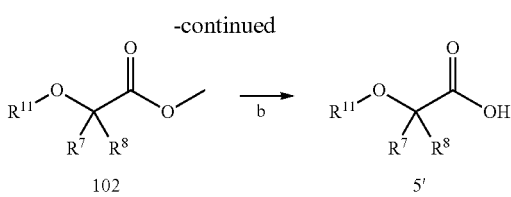

Alternatively, building block 5' used in scheme 2 and 4 can be synthesized as summarized in scheme 10. The appropriate, commercially available Grignard-reagent 110 is reacted with epoxy-ester 111 in a regio- and stereoselective manner to deliver α-hydroxy ester 112, typically under copper catalysis, e.g., copper bromide dimethyl sulfide, in an inert solvent like THF, in a temperature range of −78° C. to −20° C. Ensuing etherification is accomplished by treating the latter with a phenolic compound 101 under typical Mitsunobu-conditions, e.g., DIAD or DEAD and triphenylphosphine, in an inert solvent like THF, in a temperature range of −20° C. to RT to give 113. In case 112 is used as homochiral alcohol, this reaction takes place under clean inversion. Careful hydrolysis under standard conditions, e.g., LiOH in a mixture of water, MeOH or EtOH, and THF, in a temperature range of −20° C. to RT, delivers building block 5' without erosion of the stereochemical integrity.

Scheme 10

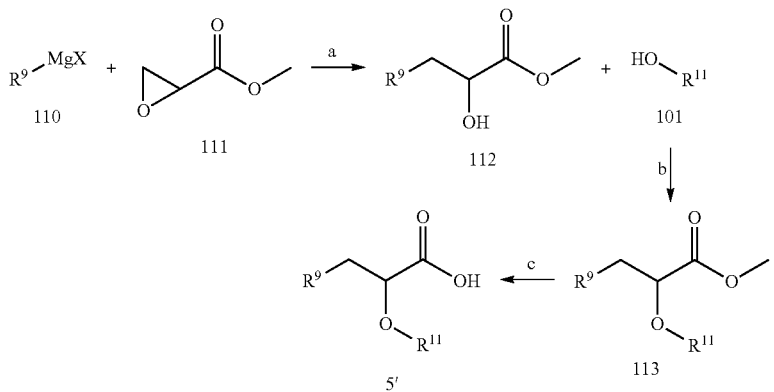

Also an embodiment of the present invention is a process to prepare a compound of formula (I) as defined above comprising the reaction of a compound of formula (II) in oxidative conditions;

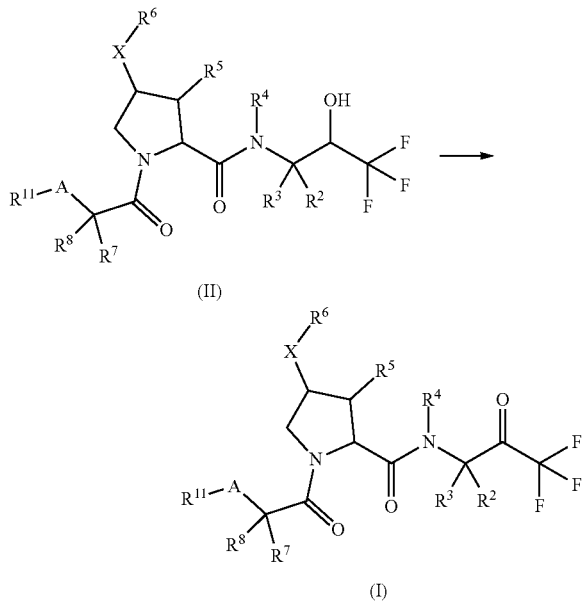

wherein $R^2$, $R^3$, $R^4$, $R^5$, $R^6$, $R^7$, $R^8$, X, A and $R^{11}$ are as defined above.

In particular, in the presence of 1,1,1-triacetoxy-1,1-dihydro-1,2-benziodoxol-3(1H)-one (Dess-Martin periodane), in a solvent like DCM between 0° C. and room temperature.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of ocular diseases, in particular HtrA1-mediated ocular diseases, more particularly wet or dry age-related macular degeneration, geographic atrophy, diabetic retinopathy, retinopathy of prematurity or polypoidal choroidal vasculopathy.

In a particular embodiment, the compounds of formula (I) or their pharmaceutically acceptable salts and esters can be used for the treatment or prophylaxis of wet or dry age-related macular degeneration, geographic atrophy, diabetic retinopathy, retinopathy of prematurity or polypoidal choroidal vasculopathy.

The present invention also relates to the use of a compound according to formula (I) as described herein for the preparation of a medicament for the treatment or prophylaxis of wet or dry age-related macular degeneration, geographic atrophy, diabetic retinopathy, retinopathy of prematurity and polypoidal choroidal vasculopathy.

Also an object of the invention is a method for the treatment or prophylaxis of wet or dry age-related macular degeneration, geographic atrophy, diabetic retinopathy, retinopathy of prematurity and polypoidal choroidal vasculopathy, which method comprises administering an effective amount of a compound according to formula (I) as described herein.

Also an embodiment of the present invention are compounds of formula (I) as described herein, when manufactured according to any one of the described processes.

Assay Procedures

Protein Purification for Use in Enzymatic Assays

Human HtrA1 protein comprising the catalytic and the PDZ domain from amino acid Asp161 up to Pro480 was expressed in BL21(DE3) cells as an N-terminal fusion protein with a 6×His-SUMO tag. The transformed cells were grown in LB medium at 37° C. until the optical density at 600 nm was between 0.6 and 0.8. Then, the temperature was decreased to 18° C. and the recombinant protein production induced by adding IPTG to a final concentration of 250 mM. Fermentation was performed over night at 18° C.

The protein was purified to homogeneity following a four-step procedure. 40 g of cells were suspended in 50 mM HEPES pH 7.8, 250 mM NaCl, 10 mM MgCl$_2$, 0.35% CHAPS, 10% glycerol containing 20 tabs per liter of EDTA-free cOmplete Protease Inhibitor (Roche) as well as 30 mg/l DNAse and Rnase. The cells were broken by a single passage through a homogenizer at 750 bar and then centrifuged at 20,000×g for 30 minutes. The clear supernatant was applied on a triple 5 ml HisTrap column (GE Healthcare) equilibrated in 50 mM HEPES pH 7.8, 500 mM NaCl, 0.35% CHAPS, 10% glycerol. After washing with stepwise increasing concentrations of imidazole (20 mM, 40 mM, 50 mM) HtrA1 fusion protein was eluted within a linear gradient from 10 to 100% of the same buffer containing 500 mM imidazole. HtrA1 containing fractions were pooled, concentrated and then applied to a Superdex S200 prep grade (XK26/100—GE Healthcare) column equilibrated in 50 mM ethanolamine pH 9.6, 500 mM NaCl, 0.35% CHAPS, 10% glycerol, 0.02% sodium azide. In order to cleave the SUMO fusion protein and to release active HtrA1, the pooled fractions from the size exclusion chromatography were blended with SUMO protease (Life Technologies) and incubated ca. 20 hours at RT. HtrA1 was isolated out of the reaction solution by chromatography on a Superdex S200 prep grade (XK26/100—GE Healthcare) column equilibrated 50 mM ethanolamine pH 9.6, 500 mM NaCl, 0.35% CHAPS, 10% glycerol, 0.02% sodium azide. Fractions containing active HtrA1 were pooled and concentrated. Following the above strategy 150 mg of the HtrA1 (catalytical domain/PDZ construct) could be purified. As shown by RP-HPLC and SDS-PAGE, >98% pure protein was obtained.

HtrA1 Enzyme Inhibition Assay

Enzyme activity is measured by observing the increase in fluorescence intensity caused by cleavage of a peptide substrate containing a fluorophore, whose emission is quenched in the intact peptide.

Assay buffer: 500 mM Tris pH 8.0, 200 mM NaCl, 0.025% CHAPS, 0.005% BSG

Enzyme: human HtrA1 Cat-PDZ, final concentration 1 nM

Substrate: Mca-Ile-Arg-Arg-Val-Ser-Tyr-Ser-Phe-Lys(Dnp)-Lys, final concentration 500 nM (from Innovagen Cat: SP-5076-1, Lot: 89584.02)

Mca=(7-Methoxycoumarin-4-yl)acetyl

Dnp=2,4-Dinitrophenyl

Final volume: 51 µl

Excitation 320 nm, emission 390 nm

After a pre-incubation of the HtrA1 protease for 30 min with compounds, substrate is added to the wells and initial RFU is measured. Upon incubation for 2 hours at RT, the enzymatic activity cleaved the substrate releasing fluorescent Mca-peptide conjugate and the final RFU value is measured. The presence of inhibitors leads to a decreased final RFU.

For the analysis ΔRFU is calculated as $RFU_{end}-RFU_{stat}$ and then percent inhibition is calculated with the following formula:

$$PCT\_Inhibition=100-100*(\Delta RFU_{compound}-\Delta RFU_{blank})/(\Delta RFU_{neg.ctr}-\Delta RFU_{blank})$$

where neg.ctrl is protease with substrate and DMSO blank is as neg. ctrl without protease compound is as neg. ctrl with test compounds at desired concentration The $IC_{50}$ is determined using a 4-point Hill-fit equation where x=concentration of test compound A=extrapolated value of the curve at effector concentration equals 0

B=extrapolated value of the curve at effector concentration equals infinite

C=concentration at the inflection point of the sigmoidal curve ($IC_{50}$)

D=Hill coefficient of slope at the inflection point of the fitted curve $$Y(x) = A + \frac{B - A_D}{1 + \left(\frac{C}{x}\right)}$$

As a counter screen the compounds are added to the protease-substrate reaction mix only after 2 h incubation, when all the substrate is turned over, to identify autofluorescent or absorbing compounds giving false positive hits.

| Example | IC50 (µM) |
|---|---|
| 1 | 0.00412 |
| 2 | 0.01050 |
| 3 | 0.00436 |
| 4 | 0.00289 |
| 5 | 0.00154 |
| 6 | 0.00133 |
| 8 | 0.00055 |
| 9 | 0.00095 |
| 10 | 0.00105 |
| 11 | 0.00127 |
| 12 | 0.05535 |
| 13 | 0.00750 |
| 14 | 0.01960 |
| 15 | 0.00895 |
| 16 | 0.00219 |
| 17 | 0.00511 |
| 18 | 0.00155 |
| 19 | 0.01480 |
| 20 | 0.00321 |
| 21 | 0.00199 |
| 22 | 0.01350 |
| 23 | 0.00601 |
| 24 | 0.00335 |

Compounds of formula (I) and their pharmaceutically acceptable salts or esters thereof as described herein have $IC_{50}$ values between 0.00001 µM and 1000 µM, particular compounds have $IC_{50}$ values between 0.0005 µM and 500 µM, further particular compounds have $IC_{50}$ values between 0.0005 µM and 50 µM, more particular compounds have $IC_{50}$ values between 0.0005 µM and 5 µM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations; lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg, can be administered either by single dose per day or per week, or by multiple doses (2 to 4) per day, or by multiple doses per week. In case of parenteral application, such as intramuscularly, intravenously, or intraocularly, the formulation can contain 0.001% to 15% by weight of medicament and the required dose, which can be between 0.01 and 25 mg, can be administered either by single dose per day, per week or per month, or by multiple doses (2 to 4) per day, or by multiple doses per week or per month. It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations: aq.=aqueous; CAS-RN=Chemical Abstracts Service Registry Number; HPLC=high performance liquid chromatography; MS=mass spectrum; sat.=saturated Examples Intermediate P-1

(2S,4R)-4-benzylsulfonyl-1-[(2-methylpropan-2-yl)oxycarbonyl]pyrrolidine-2-carboxylic Acid

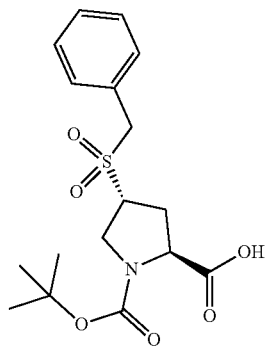 [SMILES: CC(C)(C)OC(=O)N1C[C@H](S(=O)(=O)Cc2ccccc2)C[C@H]1C(=O)O]

[A] (2S,4R)-1-tert-Butyl 2-methyl 4-(benzylthio)pyrrolidine-1,2-dicarboxylate

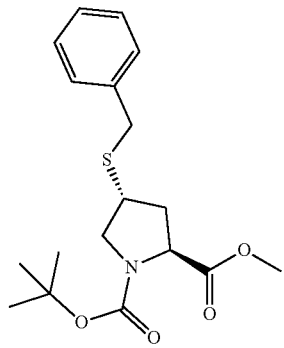 [SMILES: COC(=O)[C@@H]1C[C@@H](SCc2ccccc2)CN1C(=O)OC(C)(C)C]

In a flask, potassium tert-butoxide 1M in THF (1.9 mL, 1.9 mmol) was combined with THF (7 mL) and the resulting colorless solution was cooled to −5° C. Phenylmethanethiol (267 µL, 2.28 mmol) was added and the reaction mixture was stirred at room temperature for 15 minutes. The reaction was cooled to 0° C. and a solution of (2S,4S)-1-tert-butyl 2-methyl 4-chloropyrrolidine-1,2-dicarboxylate (CAS [169032-99-9], 0.5 g, 1.9 mmol) in DMF (7 mL) was added dropwise. The mixture was stirred at this temperature for 30 minutes at 0° C. then allowed to warm up and stirring was continued at room temperature for 3 hours. The mixture was poured into a sat. NH$_4$Cl aqueous solution and extracted with EtOAc. The organic layers were washed with a sat. NaHCO$_3$ aqueous solution and brine. Combined organics were dried over Na$_2$SO$_4$, filtered and concentrated in vacuo. The crude material was purified by silica gel flash chromatography eluting with a 10% to 80% EtOAc-heptane gradient to give the title compound (0.489 g, 73%) as a colorless oil.

[B] (2S,4R)-1-tert-Butyl 2-methyl 4-(benzylsulfonyl)pyrrolidine-1,2-dicarboxylate

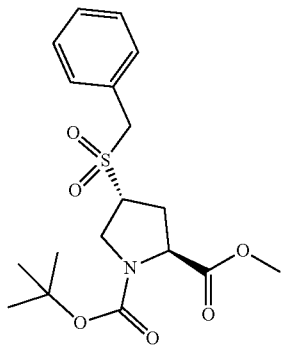 [SMILES: COC(=O)[C@@H]1C[C@@H](S(=O)(=O)Cc2ccccc2)CN1C(=O)OC(C)(C)C]

In a flask, (2S,4R)-1-tert-butyl 2-methyl 4-(benzylthio)pyrrolidine-1,2-dicarboxylate (0.483 g, 1.37 mmol) was combined with DCM (20 mL) and the resulting colorless solution was cooled to 0° C. mCPBA (0.711 g, 2.89 mmol) was added at 0° C. and the reaction mixture was stirred for 1 hour at this temperature. The mixture was poured into a sat. NaHCO$_3$ aqueous solution and extracted with DCM (2×25 mL). The organic layers were washed with brine, dried over Na$_2$SO$_4$, filtered and concentrated in vacuo. The crude material was purified by silica gel flash chromatography eluting with a 20% to 70% EtOAc-heptane gradient to give the title compound (0.454 g, 86%) as a colorless oil. MS: 284.1 (M-Boc+H$^+$).

[C] (2S,4R)-4-Benzylsulfonyl-1-[(2-methylpropan-2-yl)oxycarbonyl]pyrrolidine-2-carboxylic Acid

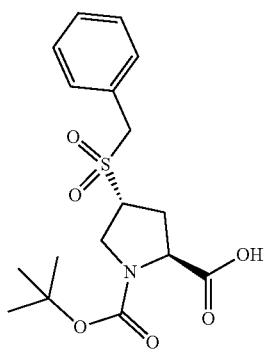 [SMILES: CC(C)(C)OC(=O)N1C[C@H](S(=O)(=O)Cc2ccccc2)C[C@H]1C(=O)O]

In a flask, (2S,4R)-1-tert-butyl 2-methyl 4-(benzylsulfonyl)pyrrolidine-1,2-dicarboxylate (0.447 g, 1.17 mmol) was combined with THF (6 mL) and methanol (3 mL) and the resulting colorless solution was cooled to 0° C. A 1M aqueous solution of LiOH (1.52 mL, 1.52 mmol) was added at 0° C. and the reaction mixture was stirred for 2 hours at this temperature. The mixture was quenched with a 1M KHSO$_4$ aqueous solution and extracted with EtOAc (2×25 mL). The organic layers were washed with brine, dried over Na$_2$SO$_4$, filtered and concentrated in vacuo to give the title compound (0.426 g, 99%) as a colorless foam. MS: 368.3 (M–H$^-$).

Intermediate P-2

(2S,4R)-4-[(4-methoxyphenyl)methylsulfonyl]-1-[(2-methylpropan-2-yl)oxycarbonyl]pyrrolidine-2-carboxylic Acid

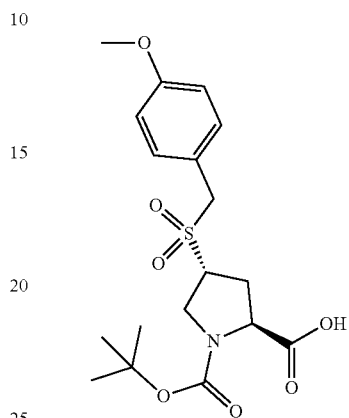

was prepared in analogy to intermediate P-1, but using in step [A] (4-methoxyphenyl)methanethiol, to give the title compound as colorless solid; MS: 300.1 (M-Boc+H$^+$).

Intermediate P-3

(2S,4R)-4-[(4-methoxyphenyl)methylsulfanyl]-1-[(2-methylpropan-2-yl)oxycarbonyl]pyrrolidine-2-carboxylic Acid

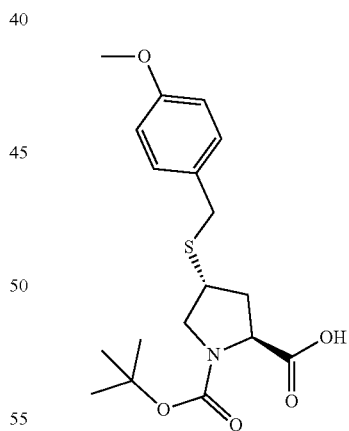

was prepared by reaction of (2S,4S)-1-tert-butyl 2-methyl 4-chloropyrrolidine-1,2-dicarboxylate and (4-methoxyphenyl)methanethiol in analogy to intermediate P-1, step [A], followed by hydrolysis of the resultant (2S,4R)-1-tert-butyl 2-methyl 4-(benzylsulfanyl)pyrrolidine-1,2-dicarboxylate in analogy to intermediate P-1, step [C].

Colorless and viscous oil; MS: 268.2 (M-Boc+H$^+$).

Intermediate A-1

(2S,4R)-4-[(4-Methoxyphenyl)methylsulfonyl]-N-[(2S,3S)-1,1,1-trifluoro-2-hydroxy-4-methylpentan-3-yl]pyrrolidine-2-carboxamide

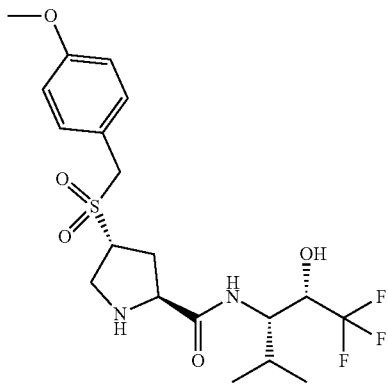 [SMILES: COc1ccc(CS(=O)(=O)[C@H]2CN[C@H](C(=O)N[C@@H](C(C)C)[C@H](O)C(F)(F)F)C2)cc1]

[A] tert-Butyl (2S,4R)-4-[(4-methoxyphenyl)methylsulfonyl]-2-[[(2S,3S)-1,1,1-trifluoro-2-hydroxy-4-methylpentan-3-yl]carbamoyl]pyrrolidine-1-carboxylate

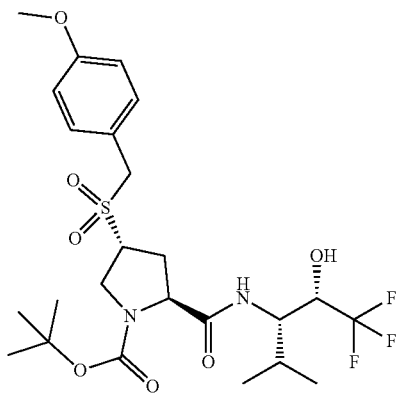 [SMILES: COc1ccc(CS(=O)(=O)[C@@H]2C[C@@H](C(=O)N[C@@H](C(C)C)[C@H](O)C(F)(F)F)N(C(=O)OC(C)(C)C)C2)cc1]

To a solution of (2S,4R)-4-[(4-methoxyphenyl)methylsulfonyl]-1-[(2-methylpropan-2-yl)oxycarbonyl]pyrrolidine-2-carboxylic acid (Intermediate P-2, 0.166 g, 0.416 mmol), (2S,3S)-3-amino-1,1,1-trifluoro-4-methylpentan-2-ol×HCl (0.086 g, 0.416 mmol) and HATU (0.190 g, 0.499 mmol) in DMF (2 mL) was added Huenig's base (0.181 mL, 1.04 mmol) and the reaction mixture stirred at room temperature for 3 hours. The mixture was diluted with EtOAc and washed with 1N HCl and brine. The organic phase was dried over Na$_2$SO$_4$, filtered and evaporated. The crude material was purified by silica gel flash chromatography eluting with a 10 to 80% EtOAc-heptane gradient to give the title compound (0.2 g, 87%) as a colorless solid. MS: 553.2 (M+H$^+$).

[B] (2S,4R)-4-[(4-Methoxyphenyl)methylsulfonyl]-N-[(2S,3S)-1,1,1-trifluoro-2-hydroxy-4-methylpentan-3-yl]pyrrolidine-2-carboxamide

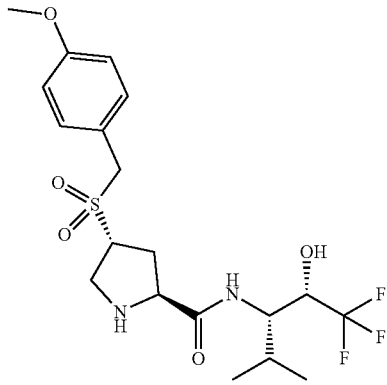 [SMILES: COc1ccc(CS(=O)(=O)[C@H]2CN[C@H](C(=O)N[C@@H](C(C)C)[C@H](O)C(F)(F)F)C2)cc1]

To a solution of tert-butyl (2S,4R)-4-[(4-methoxyphenyl)methylsulfonyl]-2-[[(2S,3S)-1,1,1-trifluoro-2-hydroxy-4-methylpentan-3-yl]carbamoyl]pyrrolidine-1-carboxylate (0.200 g, 0.362 mmol) in MeOH (2 mL) was added 4M HCl in dioxane (0.452 mL, 1.81 mmol) and the reaction mixture was stirred at room temperature overnight. The mixture was evaporated to dryness and the resulting crude material triturated with diisopropylether. The solid precipitate was filtered off and further dried under high vacuum to give the title compound (0.172 g, 97%, HCl salt) as a pale yellow solid. MS: 453.2 (M+H$^+$).

Intermediate A-2

(2S,4R)-4-[(4-Methoxyphenyl)methylsulfonyl]-N-[(2S,3S)-1,1,1-trifluoro-2-hydroxy-4-methylpentan-3-yl]pyrrolidine-2-carboxamide

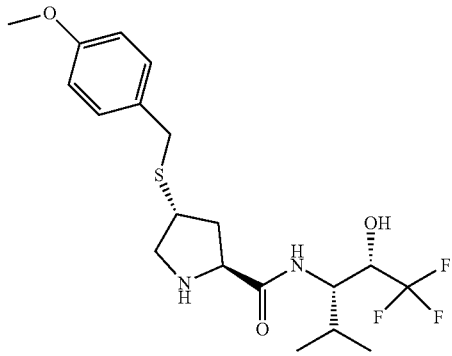 [SMILES: COc1ccc(CS[C@H]2CN[C@H](C(=O)N[C@@H](C(C)C)[C@H](O)C(F)(F)F)C2)cc1]

was prepared in analogy to intermediate A-1, but using in step [A] (2S,4R)-4-[(4-methoxyphenyl)methylsulfanyl]-1-[(2-methylpropan-2-yl)oxycarbonyl]pyrrolidine-2-carboxylic acid (Intermediate P-3), to give the title compound as a light yellow solid as hydrochloride. MS: 421.1 (M+H$^+$).

Intermediate A-3

(2S,4R)-1-[(2S)-2-Amino-3-(3-chlorophenyl)propanoyl]-4-[(4-methoxyphenyl)methylsulfonyl]-N-[(2S,3S)-1,1,1-trifluoro-2-hydroxy-4-methylpentan-3-yl]pyrrolidine-2-carboxamide

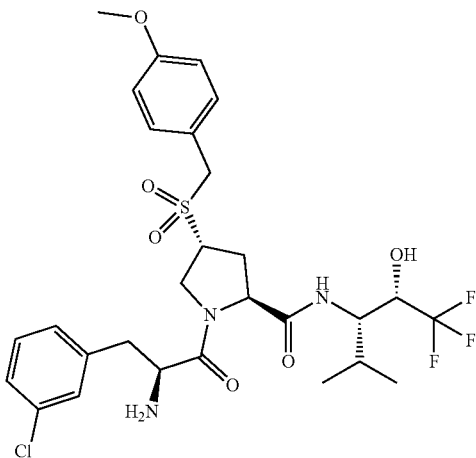 [SMILES: COc1ccc(CS(=O)(=O)[C@@H]2C[C@@H](C(=O)N[C@@H](C(C)C)[C@H](O)C(F)(F)F)N(C(=O)[C@@H](N)Cc3cccc(Cl)c3)C2)cc1]

[A] tert-Butyl N-[(2S)-3-(3-chlorophenyl)-1-[(2S,4R)-4-[(4-methoxyphenyl)methylsulfonyl]-2-[[(2S,3S)-1,1,1-trifluoro-2-hydroxy-4-methylpentan-3-yl]carbamoyl]pyrrolidin-1-yl]-1-oxopropan-2-yl]carbamate

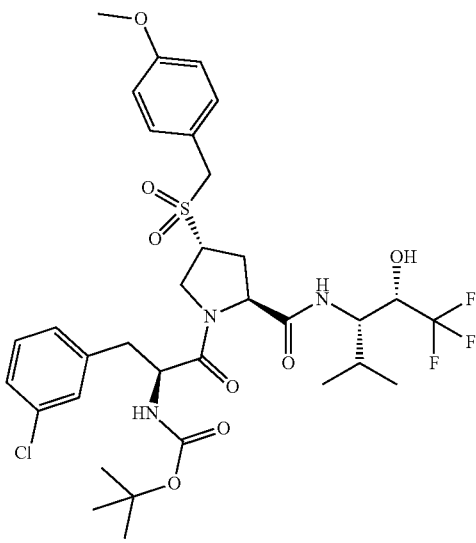 [SMILES: COc1ccc(CS(=O)(=O)[C@@H]2C[C@@H](C(=O)N[C@@H](C(C)C)[C@H](O)C(F)(F)F)N(C(=O)[C@H](Cc3cccc(Cl)c3)NC(=O)OC(C)(C)C)C2)cc1]

To a solution of (2S,4R)-4-((4-methoxybenzyl)sulfonyl)-N-((2S,3S)-1,1,1-trifluoro-2-hydroxy-4-methylpentan-3-yl)pyrrolidine-2-carboxamide×HCl (Intermediate A-1, 0.130 g, 0.266 mmol), (2S)-2-((tert-butoxycarbonyl)amino)-3-(3-chlorophenyl)propanoic acid (0.08 g, 0.266 mmol) and HATU (0.121 g, 0.319 mmol) in DMF (2 mL) was added Huenig's base (0.139 mL, 0.798 mmol) and the reaction mixture stirred at room temperature overnight. The mixture was diluted with EtOAc and washed with 1N aqueous HCl solution and brine. The organic phase was dried over Na₂SO₄, filtered and evaporated. The residue was purified by silica gel flash chromatography eluting with a 10 to 80% EtOAc-heptane gradient to give the title compound (0.148 g, 76%) as a colorless solid. MS: 734.3 (M+H⁺).

[B] (2S,4R)-1-[(2S)-2-Amino-3-(3-chlorophenyl)propanoyl]-4-[(4-methoxyphenyl)methylsulfonyl]-N-[(2S,3S)-1,1,1-trifluoro-2-hydroxy-4-methylpentan-3-yl]pyrrolidine-2-carboxamide

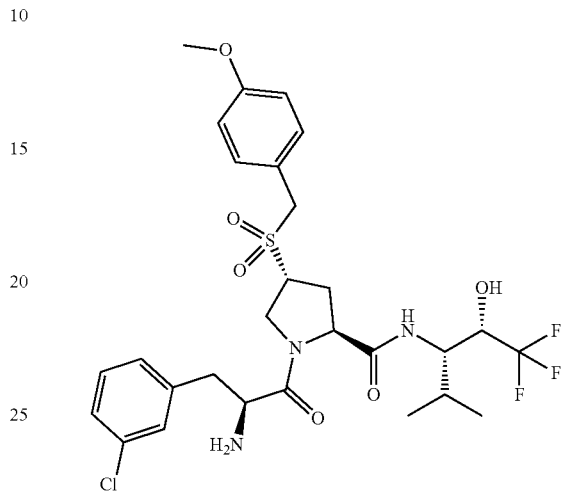

To a solution of tert-butyl N-[(2S)-3-(3-chlorophenyl)-1-[(2S,4R)-4-[(4-methoxyphenyl)methylsulfonyl]-2-[[(2S,3S)-1,1,1-trifluoro-2-hydroxy-4-methylpentan-3-yl]carbamoyl]pyrrolidin-1-yl]-1-oxopropan-2-yl]carbamate (0.148 g, 0.202 mmol) in MeOH (2 mL) was added 4M HCl in dioxane (0.252 mL, 1.01 mmol) and the reaction mixture stirred at room temperature overnight. The mixture was evaporated to dryness and triturated with diisopropylether. The solid precipitate was filtered off and further dried under high vacuum to give the title compound (0.133 g, 98%, HCl salt) as an off-white solid. MS: 634.3 (M+H⁺).

Intermediate A-4

(2S,4R)-1-[(2S)-2-Aminopropanoyl]-4-[(4-methoxyphenyl)methylsulfonyl]-N-[(2S,3S)-1,1,1-trifluoro-2-hydroxy-4-methylpentan-3-yl]pyrrolidine-2-carboxamide

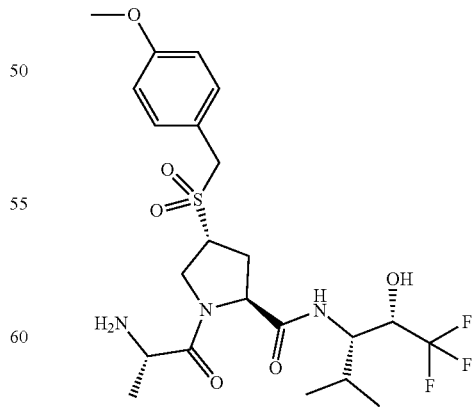

was prepared in analogy to intermediate A-3, but using in step [A] (2S)-2-(tert-butoxycarbonylamino)propanoic acid, to give the title compound as yellow solid as hydrochloride; MS: 524.2 (M+H⁺).

Intermediate A-5

(2S,4R)-1-[(2S)-2-Aminopropanoyl]-4-[(4-methoxyphenyl)methylsulfonyl]-N-[(2S,3S)-1,1,1-trifluoro-2-hydroxy-4-methylpentan-3-yl]pyrrolidine-2-carboxamide

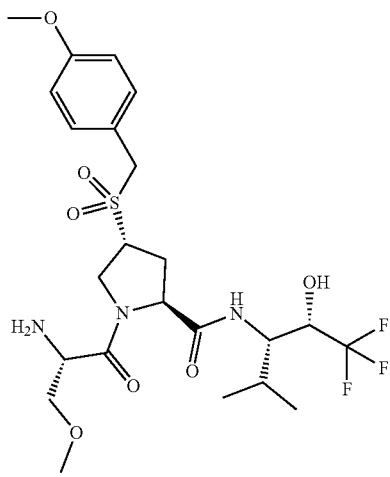 [SMILES: COC[C@H](N)C(=O)N1C[C@H](S(=O)(=O)Cc2ccc(OC)cc2)C[C@H]1C(=O)N[C@@H](C(C)C)[C@H](O)C(F)(F)F]

was prepared in analogy to intermediate A-3, but using in step [A] (2S)-2-(tert-butoxycarbonylamino)-3-methoxypropanoic acid, to give the title compound as light brown solid as hydrochloride; MS: 554.2 (M+H$^+$).

Intermediate A-6

(2S,4R)-1-[(2S)-2-Amino-3-[tert-butyl(dimethyl)silyl]oxypropanoyl]-4-[(4-methoxyphenyl)methylsulfonyl]-N-[(2S,3S)-1,1,1-trifluoro-2-hydroxy-4-methylpentan-3-yl]pyrrolidine-2-carboxamide

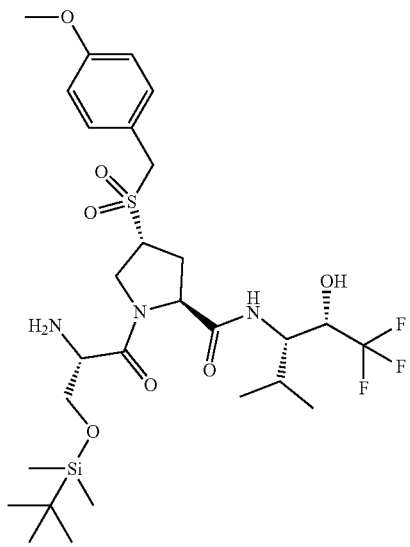 [SMILES: COc1ccc(CS(=O)(=O)[C@@H]2C[C@@H](C(=O)N[C@@H](C(C)C)[C@H](O)C(F)(F)F)N(C(=O)[C@@H](N)CO[Si](C)(C)C(C)(C)C)C2)cc1]

[A] 9H-Fluoren-9-ylmethyl N-[(2S)-3-[tert-butyl(dimethyl)silyl]oxy-1-[(2S,4R)-4-[(4-methoxyphenyl)methylsulfonyl]-2-[[(2S,3S)-1,1,1-trifluoro-2-hydroxy-4-methylpentan-3-yl]carbamoyl]pyrrolidin-1-yl]-1-oxopropan-2-yl]carbamate To a solution of (2S,4R)-4-[(4-methoxyphenyl)methylsulfonyl]-N-[(2S,3S)-1,1,1-trifluoro-2-hydroxy-4-methylpentan-3-yl]pyrrolidine-2-carboxamide hydrochloride (Intermediate A-1, 0.321 g, 0.657 mmol) (2S)-3-[tert-butyl(dimethyl)silyl]oxy-2-(9H-fluoren-9-ylmethoxycarbonylamino)propanoic acid (0.290 g, 0.657 mmol) and HATU (0.300 g, 0.788 mmol) in DMF (2 mL) cooled to 0° C. was added Huenig's base (0.573 mL, 3.28 mmol). The reaction mixture was stirred for 30 minutes, then allowed to warm up to room temperature and stirred for 2 hours. The mixture was diluted with EtOAc and washed with water and brine. The organic phase was dried over Na$_2$SO$_4$, filtered and evaporated. The residue was purified by silica gel flash chromatography eluting with a 0 to 100% EtOAc-heptane gradient to give the title compound (0.440 g, 76%) as a colorless solid. MS: 876.4 (M+H$^+$).

[B] (2S,4R)-1-[(2S)-2-Amino-3-[tert-butyl(dimethyl)silyl]oxypropanoyl]-4-[(4-methoxyphenyl)methylsulfonyl]-N-[(2S,3S)-1,1,1-trifluoro-2-hydroxy-4-methylpentan-3-yl]pyrrolidine-2-carboxamide To a solution of 9H-fluoren-9-ylmethyl N-[(2S)-3-[tert-butyl(dimethyl)silyl]oxy-1-[(2S,4R)-4-[(4-methoxyphenyl)methylsulfonyl]-2-[[(2S,3S)-1,1,1-trifluoro-2-hydroxy-4-methylpentan-3-yl]carbamoyl]pyrrolidin-1-yl]-1-oxopropan-2-yl]carbamate (0.435 g, 0.497 nmol) in DCM (4 mL) was added diethylamine (0.519 mL, 4.97 mmol) and the reaction mixture stirred at room temperature overnight. The solvent was evaporated to dryness and the residue purified by silica gel flash chromatography eluting with a 0 to 100% EtOAc-heptane gradient to give the title compound (0.276 g, 85%) as a colorless solid. MS: 654.3 (M+H$^+$).

Intermediate A-7 tert-butyl N-[[4-[(2S)-2-amino-3-[(2S,4R)-4-[(4-methoxyphenyl)methylsulfonyl]-2-[[(2S,3S)-1,1,1-trifluoro-2-hydroxy-4-methylpentan-3-yl]carbamoyl]pyrrolidin-1-yl]-3-oxopropyl]phenyl]methyl]carbamate

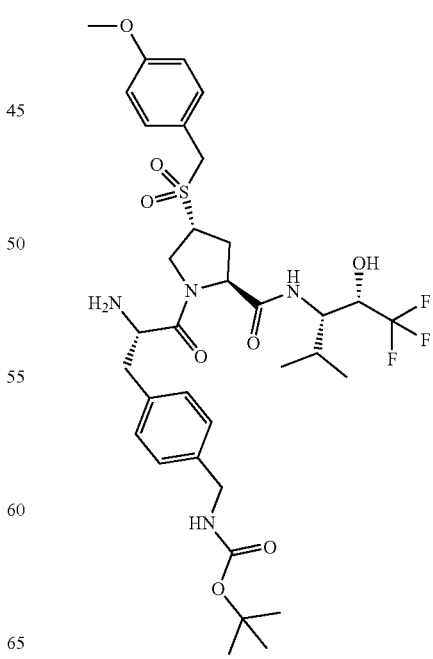

was prepared in analogy to intermediate A-6, but using in step [A] (2S)-3-[4-[(tert-butoxycarbonylamino)methyl]phenyl]-2-(9H-fluoren-9-ylmethoxycarbonyl amino)propanoic acid, to give the title compound as an off-white solid; MS: 729.3 (M+H⁺).

Intermediate O-1

(2S,4R)-4-Phenylmethoxy-N-[(2S,3S)-1,1,1-trifluoro-2-hydroxy-4-methylpentan-3-yl]pyrrolidine-2-carboxamide

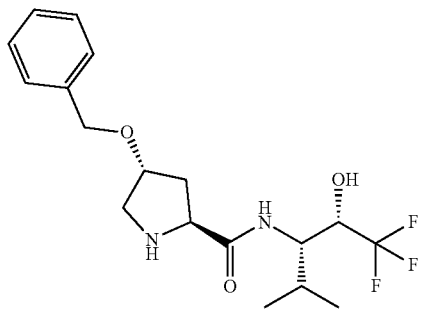 [SMILES: CC(C)[C@H](NC(=O)[C@@H]1C[C@@H](OCc2ccccc2)CN1)[C@H](O)C(F)(F)F]

was prepared in analogy to intermediate A-1, but using in step [A] Boc-O-benzyl-L-hydroxyproline, to give the title compound as off-white solid as hydrochloride; MS: 375.2 (M+H⁺).

Intermediate O-2

(2S,4R)-1-[(2S)-2-Amino-3-(3-chlorophenyl)propanoyl]-4-phenylmethoxy-N-[(2S,3S)-1,1,1-trifluoro-2-hydroxy-4-methylpentan-3-yl]pyrrolidine-2-carboxamide

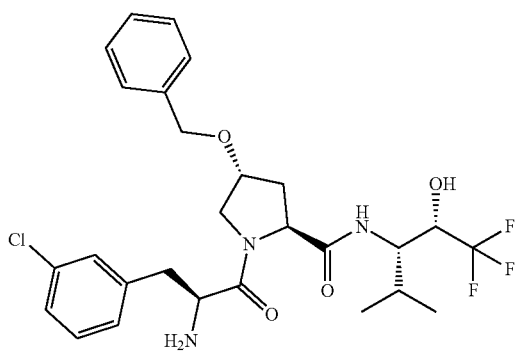 [SMILES: CC(C)[C@H](NC(=O)[C@@H]1C[C@@H](OCc2ccccc2)CN1C(=O)[C@@H](N)Cc1cccc(Cl)c1)[C@H](O)C(F)(F)F]

was prepared in analogy to intermediate A-2, but using in step [A] (2S,4R)-4-phenylmethoxy-N-[(2S,3S)-1,1,1-trifluoro-2-hydroxy-4-methylpentan-3-yl]pyrrolidine-2-carboxamide hydrochloride (Intermediate O-1), to give the title compound as light yellow solid as hydrochloride; MS: 556.2 (M+H⁺).

Intermediate F-1

(2R)-3-(3-chlorophenyl)-2-(3,5-dichlorophenoxy) propanoic Acid

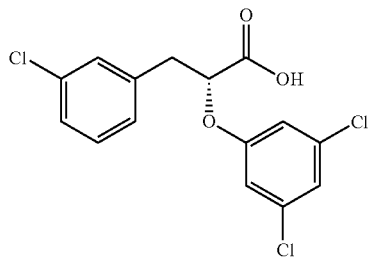 [SMILES: O=C(O)[C@@H](Cc1cccc(Cl)c1)Oc1cc(Cl)cc(Cl)c1]

[A] Methyl (2S)-3-(3-chlorophenyl)-2-hydroxypropanoate

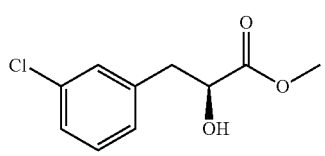

In a flask, (S)-methyl oxirane-2-carboxylate (0.4 g, 3.92 mmol) and copper bromide dimethyl sulfide (0.2 g, 0.980 mmol) were combined with THF (25 mL) and cooled to −35° C. Then, (3-chlorophenyl)magnesium bromide (7.84 mL, 7.84 mmol) was added dropwise over 15 minutes while keeping the temperature below −33° C. The reaction mixture was slowly warmed up to −25° C. The mixture was quenched with a sat. NH₄Cl aqueous solution at −20° C. and extracted with EtOAc. The organic layer was washed with water, dried over Na₂SO₄, filtered and evaporated to dryness. The crude material was purified by silica gel flash chromatography eluting with a 0 to 35% EtOAc-heptane gradient to give the title compound (0.615 g, 73%) as a colorless oil.

[B] Methyl (2R)-3-(3-chlorophenyl)-2-(3,5-dichlorophenoxy)propanoate

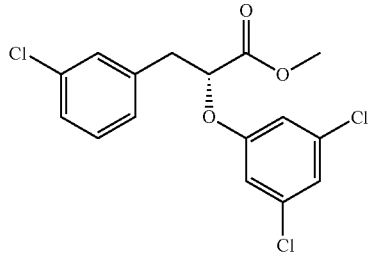 [SMILES: COC(=O)[C@@H](Cc1cccc(Cl)c1)Oc1cc(Cl)cc(Cl)c1]

In a flask, methyl (2S)-3-(3-chlorophenyl)-2-hydroxypropanoate (0.611 g, 2.85 mmol) and 3,5-dichlorophenol (0.487 g, 2.99 mmol) were combined with THF (11 mL) and cooled at −10° C. Triphenylphosphine (0.971 g, 3.7 mmol) and (E)-diisopropyl diazene-1,2-dicarboxylate (726 µL, 3.7 mmol) were subsequently added and the reaction mixture was stirred at 0° C. for 1.5 hours. The mixture was quenched with a 0.5 N aqueous HCl solution and extracted with EtOAc. The organic layer was washed with brine, dried over Na$_2$SO$_4$, filtered and evaporated to dryness. The crude material was purified by silica gel flash chromatography eluting with a 0 to 15% EtOAc-heptane gradient to give the title compound (0.763 g, 70%) as a light yellow oil.

[C] (2R)-3-(3-Chlorophenyl)-2-(3,5-dichlorophenoxy)propanoic Acid

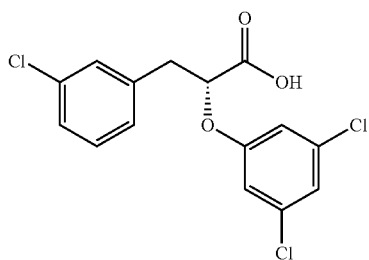 [SMILES: O=C(O)[C@@H](Cc1cccc(Cl)c1)Oc1cc(Cl)cc(Cl)c1]

In a flask, methyl (2R)-3-(3-chlorophenyl)-2-(3,5-dichlorophenoxy)propanoate (0.763 g, 2.12 mmol) was combined with THF (5 mL) and MeOH (2 mL) and cooled to 0° C. Lithium hydroxide (0.127 g, 5.3 mmol) in water (1 mL) was added and the reaction mixture stirred for 2 hours. The mixture was quenched with a 0.5 N aqueous HCl solution and extracted with EtOAc. The organic layer was washed with water until pH>2, over Na$_2$SO$_4$, filtered and evaporated to dryness. The residue was recrystallized from EtOAc/heptane to give the title compound (0.668 g, 91%) as a white crystalline solid. MS: 343.2 (M−H$^-$).

Intermediate F-2

(2R)-3-(3-Chlorophenyl)-2-(5-chloropyridin-3-yl)oxypropanoic Acid

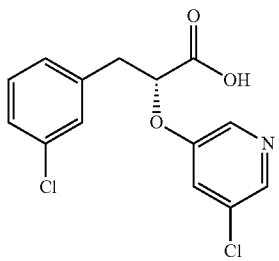 [SMILES: O=C(O)[C@@H](Cc1cccc(Cl)c1)Oc1cncc(Cl)c1]

was prepared in analogy to intermediate F-1, but using in step [B] 5-chloropyridin-3-ol and replacing THF by DCM as solvent, to give the title compound as a white foam. MS: 312.1 (M+H$^+$).

Intermediate F-3

(2R)-2-(3,5-Dichlorophenoxy)-3-phenylpropanoic Acid

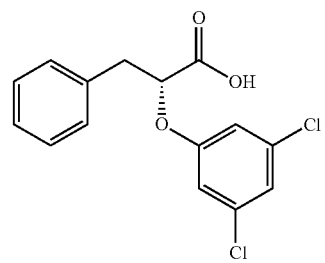 [SMILES: O=C(O)[C@@H](Cc1ccccc1)Oc1cc(Cl)cc(Cl)c1]

[A] Methyl (2R)-2-(3,5-dichlorophenoxy)-3-phenylpropanoate

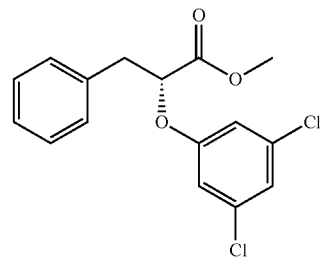 [SMILES: COC(=O)[C@@H](Cc1ccccc1)Oc1cc(Cl)cc(Cl)c1]

A solution of DIAD (0.360 g, 1.78 mmol) in THF (1 mL) was added dropwise to a mixture of methyl (2S)-2-hydroxy-3-phenyl-propanoate (0.15 g, 0.832 mmmol), 3,5-dichlorophenol (0.163 g, 1 mmol) and triphenylphosphine (0.431 g, 1.64 mmol) in THF (1.5 mL) at 0° C. under Ar. The mixture was then stirred at room temperature for 5 hours. The mixture was diluted with EtOAc, poured into water (5 mL) and the aqueous layer was extracted with EtOAc (2×15 mL). Combined organics were washed with brine, dried over Na$_2$SO$_4$, filtered and evaporated to dryness. The yellow oily residue was taken up in heptane and the white solid precipitate was filtered off. The mother liquors were evaporated to dryness and the resulting material purified by silica gel flash chromatography eluting with a 0 to 20% EtOAc-heptane gradient to give the title compound (0.135 g, 35%) as a yellow solid.

[B] (2R)-2-(3,5-Dichlorophenoxy)-3-phenylpropanoic Acid

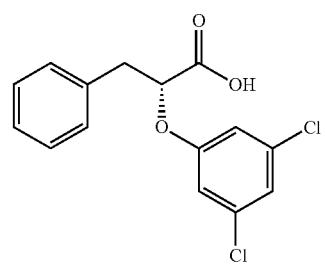 [SMILES: O=C(O)[C@@H](Cc1ccccc1)Oc1cc(Cl)cc(Cl)c1]

To a solution of methyl (2R)-2-(3,5-dichlorophenoxy)-3-phenylpropanoate (0.135 g, 0.415 mmol) in THF (1 mL) was added a 1M solution of LiOH in H$_2$O (0.623 mL, 0.623 mmol) and the reaction mixture was stirred at room temperature for 8 hours. The mixture was acidified with a 1M HCl solution (1 mL) and extracted with EtOAc (2×5 mL). Combined organics were washed with brine, dried over Na$_2$SO$_4$, filtered and evaporated to dryness to give the title compound (0.112 g, 78%) as an off-white solid. MS: 309.1 (M−H$^-$).

or (2R)-2-(3,5-Dichlorophenoxy)-3-phenylpropanoic Acid

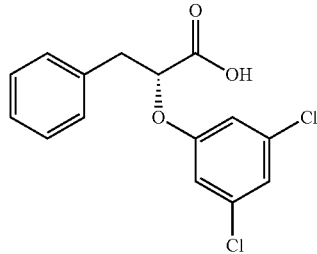 [SMILES: O=C(O)[C@@H](Cc1ccccc1)Oc1cc(Cl)cc(Cl)c1]

was prepared in analogy to intermediate F-1, but using in step [A] chlorophenylmagnesium bromide, to give the title compound as off-white solid. MS: 309.1 (M−H$^-$).

Example 1

N-[(2S)-3-(3-Chlorophenyl)-1-[(2S,4R)-4-[(4-methoxyphenyl)methylsulfonyl]-2-[[(3S)-1,1,1-trifluoro-4-methyl-2-oxopentan-3-yl]carbamoyl]pyrrolidin-1-yl]-1-oxopropan-2-yl]pyridine-2-carboxamide

[A] N-[(2S)-3-(3-Chlorophenyl)-1-[(2S,4R)-4-[(4-methoxyphenyl)methylsulfonyl]-2-[[(2S,3S)-1,1,1-trifluoro-2-hydroxy-4-methylpentan-3-yl]carbamoyl]pyrrolidin-1-yl]-1-oxopropan-2-yl]pyridine-2-carboxamide In a round-bottomed flask, (2S,4R)-1-((S)-2-amino-3-(3-chlorophenyl)propanoyl)-4-((4-methoxybenzyl)sulfonyl)-N-((2S,3S)-1,1,1-trifluoro-2-hydroxy-4-methylpentan-3-yl)pyrrolidine-2-carboxamide hydrochloride (Intermediate A-3, 0.040 g, 0.060 mmol), picolinic acid (0.007 g, 0.060 mmol) and HATU (0.027 g, 0.072 mmol) were dissolved in DMF (1 mL) and the mixture cooled to 0° C. Huenig's base (0.031 mL, 0.179 mmol) was added to the reaction mixture which was stirred at this temperature for 10 min, then allowed to warm up to room temperature and stirring was continued for 3 hours. The mixture was diluted with EtOAc and washed with 1N HCl and brine. The organic phase was dried over Na$_2$SO$_4$, filtered and evaporated. The residue was purified by silica gel flash chromatography eluting with a 10 to 100% EtOAc-heptane gradient to give the title compound (0.035 g, 79%) as a colorless solid. MS: 739.4 (M+H$^+$).

[B] N-[(2S)-3-(3-Chlorophenyl)-1-[(2S,4R)-4-[(4-methoxyphenyl)methylsulfonyl]-2-[[(3S)-1,1,1-trifluoro-4-methyl-2-oxopentan-3-yl]carbamoyl]pyrrolidin-1-yl]-1-oxopropan-2-yl]pyridine-2-carboxamide

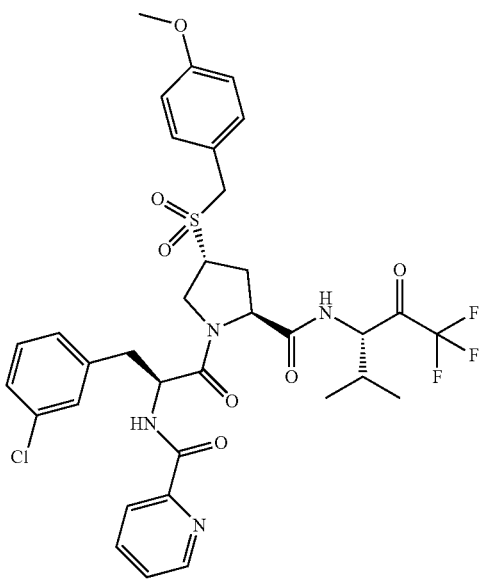 [SMILES: COc1ccc(CS(=O)(=O)[C@@H]2C[C@@H](C(=O)N[C@H](C(=O)C(F)(F)F)C(C)C)N(C(=O)[C@H](Cc3cccc(Cl)c3)NC(=O)c3ccccn3)C2)cc1]

To a suspension of N-[(2S)-3-(3-chlorophenyl)-1-[(2S,4R)-4-[(4-methoxyphenyl)methylsulfonyl]-2-[[(2S,3S)-1,1,1-trifluoro-2-hydroxy-4-methylpentan-3-yl]carbamoyl]pyrrolidin-1-yl]-1-oxopropan-2-yl]pyridine-2-carboxamide (0.032 g, 0.043 mmol) in DCM (1 mL) was added a 15% Dess-Martin periodinane in DCM solution (0.135 mL, 0.065 mmol) and the reaction mixture stirred at room temperature for 4 hours. The mixture was diluted with DCM and washed with a saturated $NH_4Cl$ aqueous solution and brine. The organic phase was dried over $Na_2SO_4$, filtered and evaporated. The residue was purified by silica gel flash chromatography, eluting with a 10-80% EtOAc-heptane gradient to give the title compound (0.021 g, 66%) as a colorless solid. MS: 737.3 (M+H⁺).

The following examples listed in Table 1 were prepared in analogy to the procedures described for the preparation of example 1 by using the indicated intermediate and carboxylic acid in step [A]

TABLE 1

| Ex | Name<br>Structure<br>Aspect | Reactant to be used in step [A] | MS (M + H⁺) |
|---|---|---|---|
| 2 | N-[(2S)-3-(3-chlorophenyl)-1-[(2S,4R)-4-[(4-methoxy-phenyl)methylsulfonyl]-2-[[(3S)-1,1,1-trifluoro-4-methyl-2-oxopentan-3-yl]carbamoyl]pyrrolidin-1-yl]-1-oxopropan-2-yl]pyrazine-2-carboxamide<br>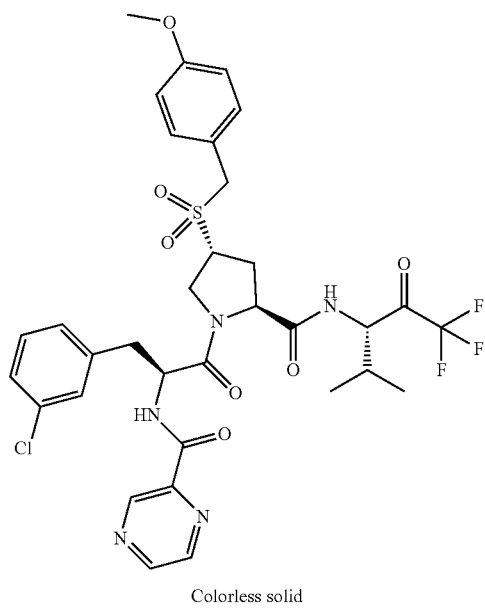 [SMILES: COc1ccc(CS(=O)(=O)[C@@H]2C[C@@H](C(=O)N[C@H](C(=O)C(F)(F)F)C(C)C)N(C(=O)[C@H](Cc3cccc(Cl)c3)NC(=O)c3cnccn3)C2)cc1]<br>Colorless solid | Intermediate A-3 and pyrazine-2-carboxylic acid | 738.4 |

TABLE 1-continued

| Ex | Name / Structure / Aspect | Reactant to be used in step [A] | MS (M + H⁺) |
|---|---|---|---|
| 3 | (2S,4R)-1-[(2S)-2-[[2-(3-chlorophenyl)-2,2-difluoroacetyl]amino]-propanoyl]-4-[(4-methoxyphenyl)methylsulfonyl]-N-[(3S)-1,1,1-trifluoro-4-methyl-2-oxopentan-3-yl]pyrrolidine-2-carboxamide<br />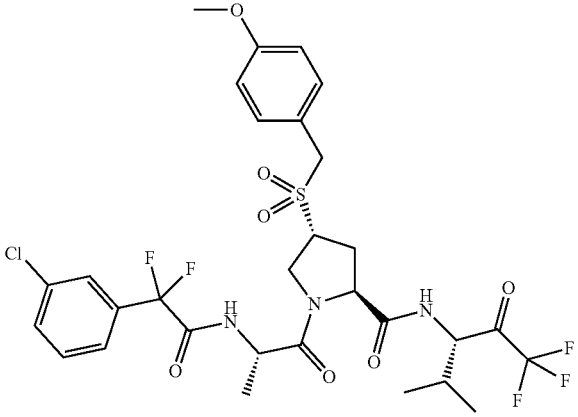<br />Colorless solid | Intermediate A-4 and 2-(3-chlorophenyl)-2,2-difluoro-acetic acid | 710.2 |
| 4 | (2S,4R)-1-[(2S)-2-[[2,2-difluoro-2-[2-(trifluoromethyl)phenyl]acetyl]-amino]propannoyl]-4-[(4-methoxyphenyl)methylsulfonyl]-N-[(3S)-1,1,1-trifluoro-4-methyl-2-oxopentan-3-yl]pyrrolidine-2-carboxamide<br />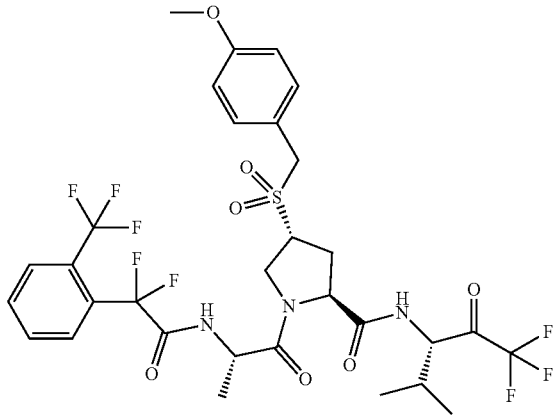<br />Colorless solid | Intermediate A-4 and 2,2-difluoro-2-[2-(trifluoro-methyl)phenyl]acetic acid | 744.2 |

TABLE 1-continued

| Ex | Name Structure Aspect | Reactant to be used in step [A] | MS (M + H+) |
|---|---|---|---|
| 5 | (2S,4R)-1-[(2S)-2-[[2-(3-chlorophenyl)-2,2-difluoroacetyl]amino]-3-methoxypropanoyl]-4-[(4-methoxyphenyl)methylsulfonyl]-N-[(3S)-1,1,1-trifluoro-4-methyl-2-oxopentan-3-yl]pyrrolidine-2-carboxamide<br>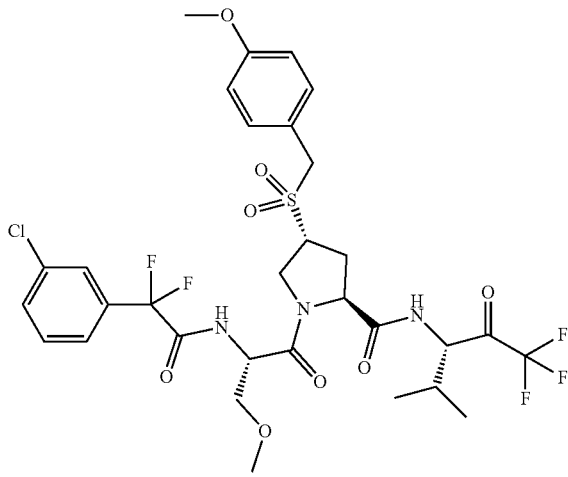<br>Colorless solid | Intermediate A-5 and 2-(3-chlorophenyl)-2,2-difluoro-acetic acid | 740.2 |
| 6 | (2S,4R)-1-[(2S)-2-[[2,2-difluoro-2[2-(trifluoromethyl)phenyl-acetyl]amino]-3-methoxypropanoyl]-4-[(4-methoxyphenyl)-methylsulfonyl]-N-[(3S)-1,1,1-trifluoro-4-methyl-2-oxopentan-3-yl]-pyrrolidine-2-carboxamide<br>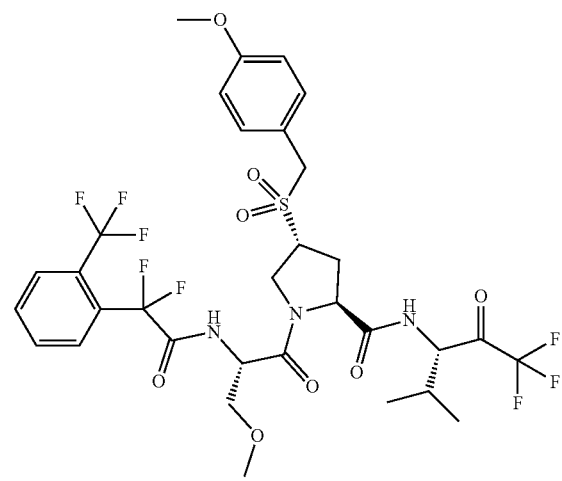<br>Colorless solid | Intermediate A-5 and 2,2-difluoro-2-[2-(trifluoro-methyl)phenyl]acetic acid | 774.2 |

TABLE 1-continued

| Ex | Name Structure Aspect | Reactant to be used in step [A] | MS (M + H+) |
|---|---|---|---|
| 7 | (2S,4R)-1-[(2S)-3-[tert-butyl(dimethyl)silyl]oxy-2-[[2-(3-chlorophenyl)-2,2-difluoroacetyl]amino]propanoyl]-4-[(4-methoxyphenyl)methylsulfonyl]-N-[(3S)-1,1,1-trifluoro-4-methyl-2-oxopentan-3-yl]-pyrrolidine-2-carboxamide<br />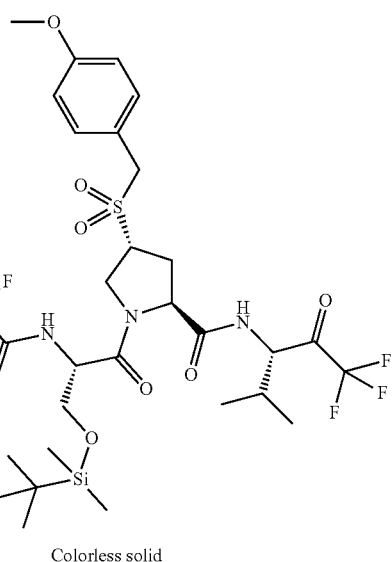<br />Colorless solid | Intermediate A-6 and 2-(3-chlorophenyl)-2,2-difluoro-acetic acid | 840.3 |
| 8 | tert-butyl N-[[4-[(2S)-2-[[2-(3-chlorophenyl)-2,2-difluoroacetyl]-amino]-3-[(2S,4R)-4-[(4-methoxyphenyl)methylsulfonyl]-2-[[(3S)-1,1,1-trifluoro-4-methyl-2-oxopentan-3-yl]carbamoyl]-pyrrolidin-1-yl]-3-oxopropyl]phenyl]methyl]carbamate<br />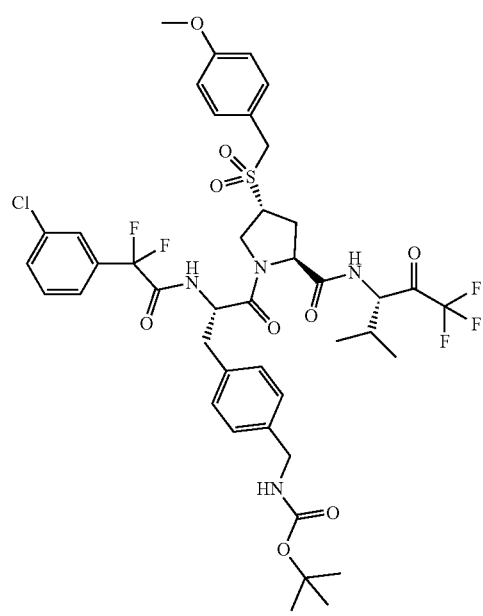<br />Colorless solid | Intermediate A-7 and 2-(3-chlorophenyl)-2,2-difluoro-acetic acid | (M − tBu + H+) = 859.1 |

TABLE 1-continued

| Ex | Name Structure Aspect | Reactant to be used in step [A] | MS (M + H⁺) |
|---|---|---|---|
| 9 | tert-butyl N-[[4-[(2S)-2-[(3-chlorobenzoyl)amino]-3-[(2S, 4R)-4-[(4-methoxyphenyl)methylsulfonyl]-2-[[(3S)-1,1,1-trifluoro-4-methyl-2-oxopentan-3-yl]carbamoyl]pyrrolidin-1-yl]-3-oxopropyl]phenyl]methyl]carbamate<br>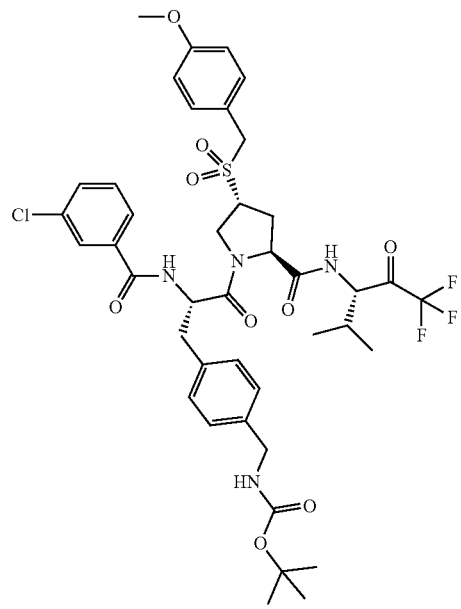<br>Colorless solid | Intermediate A-7 and 3-chlorobenzoic acid | (M − H⁻) = 863.4 |
| 10 | tert-butyl N-[[4-[(2S)-2-[[2,2-difluoro-2-[2-(trifluoromethyl)-phenyl]acetyl]amino]-3-[(2S,4R)-4-[(4-methoxyphenyl)-methylsulfonyl]-2[[(3S)-1,1,1-trifluoro-4-methyl-2-oxopentan-3-yl]carbamoyl]-pyrrolidin-1-yl]-3-oxopropyl]-phenyl]methyl]carbamate<br>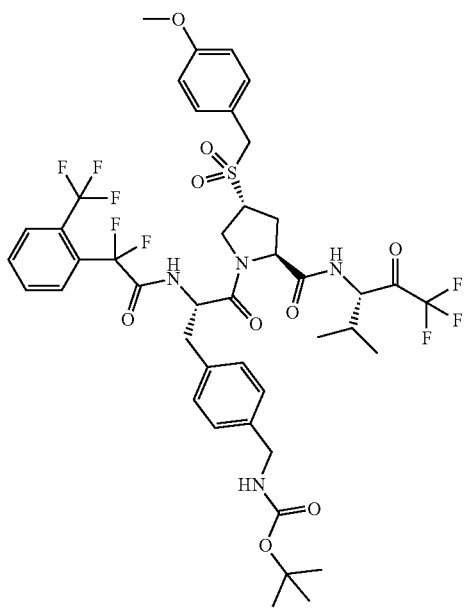<br>Colorless solid | Intermediate A-7 and 2,2-difluoro-2-[2-(trifluoromethyl)phenyl]acetic acid | (M − tBu + H⁺) = 893.4 |

TABLE 1-continued

| Ex | Name / Structure / Aspect | Reactant to be used in step [A] | MS (M + H⁺) |
|---|---|---|---|
| 11 | tert-butyl N-[[4-[(2S)-2-[[1-(4-chlorophenyl)cyclopentanecarbonyl]-amino]-3-[(2S,4R)-4-[(4-methoxyphenyl)methylsulfonyl]-2-[[(3S)-1,1,1-trifluoro-4-methyl-2-oxopentan-3-yl]carbamoyl]pyrrolidin-1-yl]-3-oxopropyl]phenyl]methyl]carbamate<br>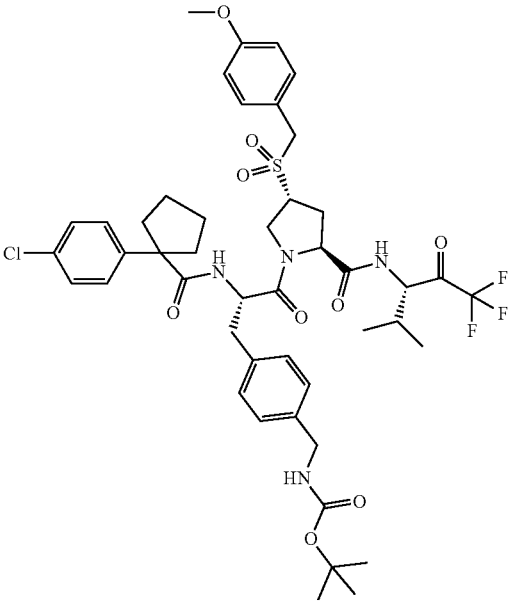<br>Colorless solid | Intermediate A-7 and 1-(4-chlorophenyl)cyclo-pentanecarboxylic acid | (M − tBu + H⁺) = 877.4 |
| 12 | (2S,4R)-1-[2-(3,5-dichlorophenoxy)acetyl]-4-[(4-methoxyphenyl)-methylsulfonyl]-N-[(3S)-1,1,1-trifluoro-4-methyl-2-oxopentan-3-yl]pyrrolidine-2-carboxamide<br>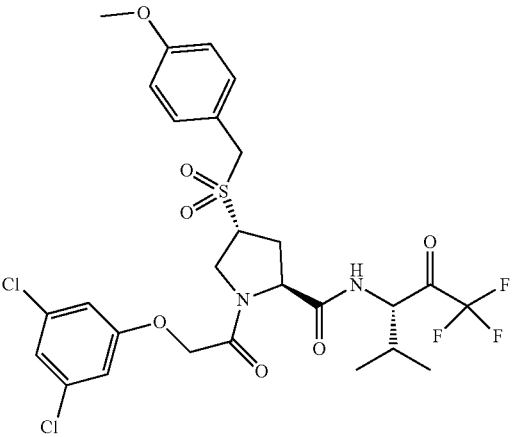<br>Colorless solid | Intermediate A-1 and 2-(3,5-dichlorophenoxy) acetic acid | 653.2 |

TABLE 1-continued

| Ex | Name<br>Structure<br>Aspect | Reactant to be used in step [A] | MS (M + H⁺) |
|---|---|---|---|
| 13 | (2S,4R)-1-[2-(3,5-dichlorophenoxy)acetyl]-4-[(4-methoxyphenyl)-methylsulfanyl]-N-[(3S)-1,1,1-trifluoro-4-methyl-2-oxopentan-3-yl]pyrrolidine-2-carboxamide<br><br>Colorless solid | Intermediate A-2 and 2-(3,5-dichlorophenoxy)-acetic acid | 623.2 |
| 14 | (2S,4R)-1-[3-(3,4-dichlorophenyl)propanoyl]-4-phenylmethoxy-N-[(3S)-1,1,1-trifluoro-4-methyl-2-oxopentan-3-yl]pyrrolidine-2-carboxamide<br><br>Colorless oil | Intermediate O-1 and 3-(3,4-dichlorophenyl) propanoic acid | 573.1 |
| 15 | (2S,4R)-1-[2-(3,5-dichlorophenoxy)acetyl]-4-phenylmethoxy-N-[(3S)-1,1,1-trifluoro-4-methyl-2-oxopentan-3-yl]pyrrolidine-2-carboxamide<br><br>Colorless solid | Intermediate O-1 and 2-(3,5 dichlorophenoxy)acetic acid | 575.1 |

TABLE 1-continued

| Ex | Name Structure Aspect | Reactant to be used in step [A] | MS (M + H⁺) |
|---|---|---|---|
| 16 | N-[(2S)-3-(3-chlorophenyl)-1-oxo-1-[(2S,4R)-4-phenylmethoxy-2-[[(3S)-1,1,1-trifluoro-4-methyl-2-oxopentan-3-yl]carbamoyl]-pyrrolidin-1-yl]propan-2-yl]pyridine-2-carboxamide<br>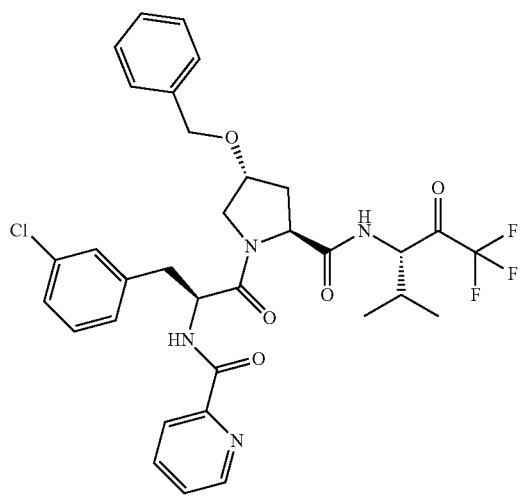<br>Colorless solid | Intermediate O-2 and pyridine-2-carboxylic acid | 659.2 |
| 17 | N-((S)-1-((2S,4R)-4-(benzyloxy)-2-(((S)-1,1,1-trifluoro-4-methyl-2-oxopentan-3-yl)carbamoyl)pyrrolidin-1-yl)-3-(3-chlorophenyl)-1-oxopropan-2-yl)pyrazine-2-carboxamide<br>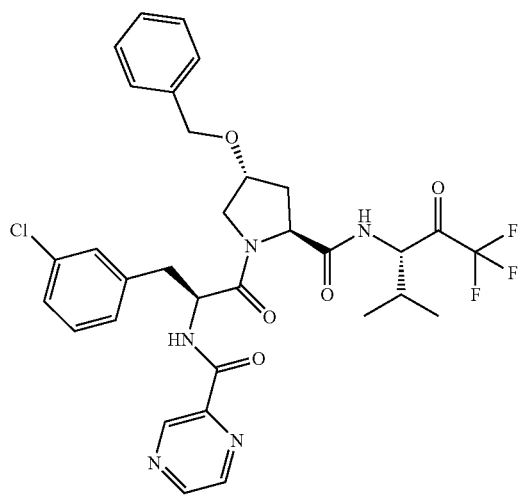<br>Colorless solid | Intermediate O-2 and pyrazine-2-carboxylic acid | 660.4 |

TABLE 1-continued

| Ex | Name<br>Structure<br>Aspect | Reactant to be used in step [A] | MS (M + H+) |
|---|---|---|---|
| 18 | (2S,4R)-1-[(2R)-2-(3,5-dichlorophenoxy)-3-phenylpropanoyl]-4-phenylmethoxy-N-[(3S)-1,1,1-trifluoro-4-methyl-2-oxopentan-3-yl]pyrrolidine-2-carboxamide<br>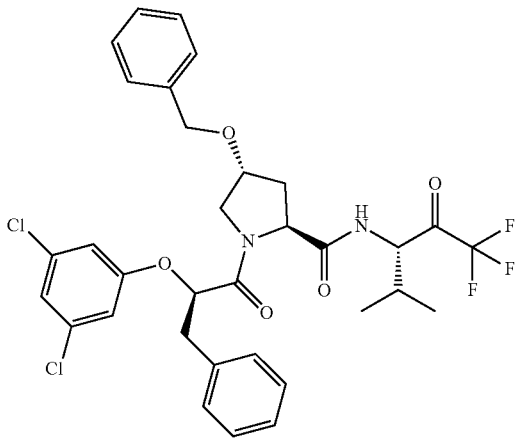<br>Colorless solid | Intermediate O-1 and (2R)-2-(3,5-dichlorophenoxy)-3-phenylpropanic acid<br><br>(Intermediate F-3) | 665.2 |

Example 19

(2S,4R)-1-[(2S)-2-[(5-Chlorothiophen-2-yl)sulfonylamino]-3-methoxypropanoyl]-4-[(4-methoxyphenyl)methylsulfonyl]-N-[(3S)-1,1,1-trifluoro-4-methyl-2-oxopentan-3-yl]pyrrolidine-2-carboxamide

[A] (2S,4R)-1-[(2S)-2-[(5-Chlorothiophen-2-yl)sulfonylamino]-3-methoxypropanoyl]-4-[(4-methoxyphenyl)methylsulfonyl]-N-[(2S,3S)-1,1,1-trifluoro-2-hydroxy-4-methylpentan-3-yl]pyrrolidine-2-carboxamide

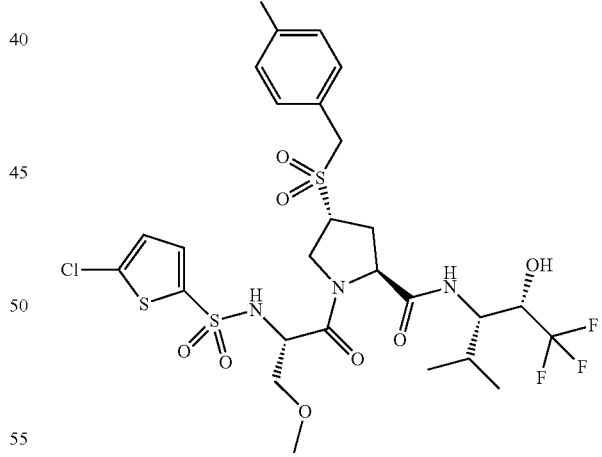

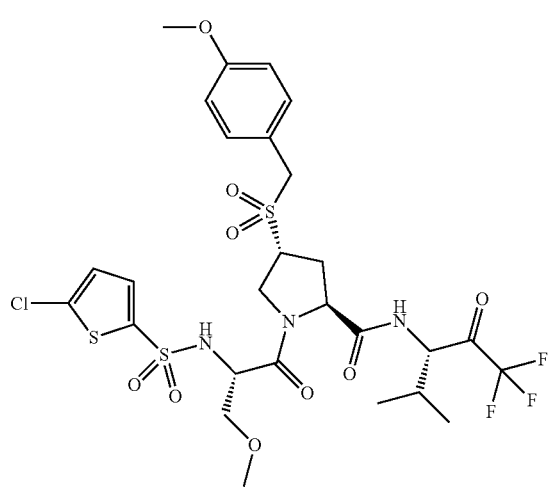 [SMILES: COC[C@H](NS(=O)(=O)c1ccc(Cl)s1)C(=O)N1C[C@H](S(=O)(=O)Cc2ccc(OC)cc2)C[C@H]1C(=O)N[C@H](C(=O)C(F)(F)F)C(C)C]

To a solution of (2S,4R)-1-[(2S)-2-aminopropanoyl]-4-[(4-methoxyphenyl)methylsulfonyl]-N-[(2S,3S)-1,1,1-trifluoro-2-hydroxy-4-methylpentan-3-yl]pyrrolidine-2-carboxamide×HCl (Intermediate A-5, 0.050 g, 0.085 mmol) in DCM (1 mL) cooled to 0° C. was added Huenig's base (0.044 mL, 0.254 mmol), followed by 5-chlorothiophene-2-sulfonyl chloride (0.022 g, 0.102 mmol). The reaction was allowed to warm to room temperature and stirring was continued for 20 hours. The mixture was diluted with DCM, poured into a sat. NH$_4$Cl aq. solution and the aqueous layer was extracted with DCM. The combined organics were washed with brine, dried over Na$_2$SO$_4$, filtered, and evaporated to dryness. The residue was purified by silica gel flash chromatography, eluting with a 0-20% EtOAc-heptane gradient gradient to give the title compound (0.034 g, 55%) as a light brown solid. MS: 734.3 (M+H$^+$).

[B] (2S,4R)-1-[(2S)-2-[(5-Chlorothiophen-2-yl)sulfonylamino]-3-methoxypropanoyl]-4-[(4-methoxyphenyl)methylsulfonyl]-N-[(3S)-1,1,1-trifluoro-4-methyl-2-oxopentan-3-yl]pyrrolidine-2-carboxamide

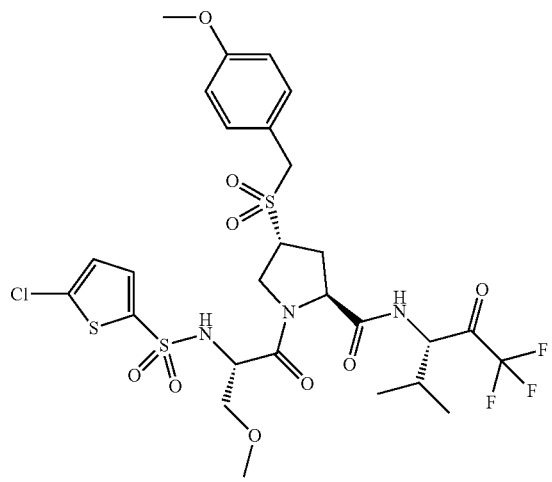 [SMILES: COC[C@H](NS(=O)(=O)c1ccc(Cl)s1)C(=O)N1C[C@H](S(=O)(=O)Cc2ccc(OC)cc2)C[C@H]1C(=O)N[C@H](C(=O)C(F)(F)F)C(C)C]

was prepared in analogy to Example 1 [B], to give the title compound as white solid. MS: 732.3 (M+H$^+$).

Example 20

(2S,4R)-1-[(2S)-2-[[2-(3-Chlorophenyl)-2,2-difluoroacetyl]amino]-3-hydroxypropanoyl]-4-[(4-methoxyphenyl)methylsulfonyl]-N-[(3S)-1,1,1-trifluoro-4-methyl-2-oxopentan-3-yl]pyrrolidine-2-carboxamide

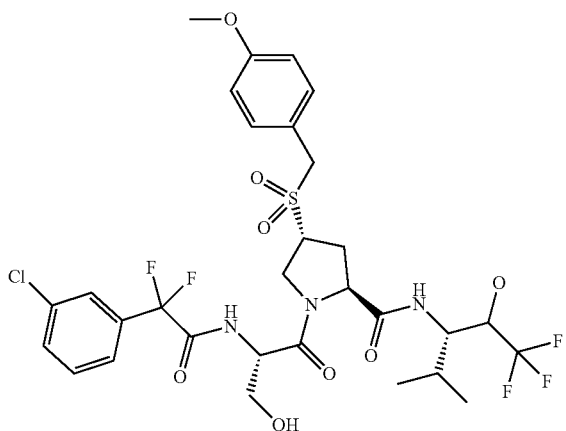 [SMILES: COc1ccc(CS(=O)(=O)[C@@H]2C[C@@H](C(=O)N[C@@H](C(C)C)C(O)C(F)(F)F)N(C(=O)[C@H](CO)NC(=O)C(F)(F)c3cccc(Cl)c3)C2)cc1]

To a solution of (2S,4R)-1-[(2S)-3-[tert-butyl(dimethyl)silyl]oxy-2-[[2-(3-chlorophenyl)-2,2-difluoroacetyl]amino]propanoyl]-4-[(4-methoxyphenyl)methylsulfonyl]-N-[(3S)-1,1,1-trifluoro-4-methyl-2-oxopentan-3-yl]pyrrolidine-2-carboxamide (Example 7, 0.022 g, 0.026 mmol) in THF (1 mL) and water (150 µL) cooled at 0° C. was added 4M HCl in dioxane (98.2 µL, 0.393 mmol) and the reaction mixture was stirred at this temperature for 4 hours. The mixture was poured into water (2.5 mL) and extracted with EtOAc (2×10 mL). The combined organic layers were washed with brine, dried over Na$_2$SO$_4$, and concentrated in vacuo. The residue was triturated in heptane with a few drops of ethyl acetate, filtered and further dried under high vacuum to give the title compound (0.17 g, 87%) as a colorless solid. MS: 726.2 (M+H$^+$).

Example 21

(2S,4R)-1-[(2S)-3-[4-(Aminomethyl)phenyl]-2-[[2-(3-chlorophenyl)-2,2-difluoroacetyl]amino]propanoyl]-4-[(4-methoxyphenyl)methylsulfonyl]-N-[(3S)-1,1,1-trifluoro-4-methyl-2-oxopentan-3-yl]pyrrolidine-2-carboxamide

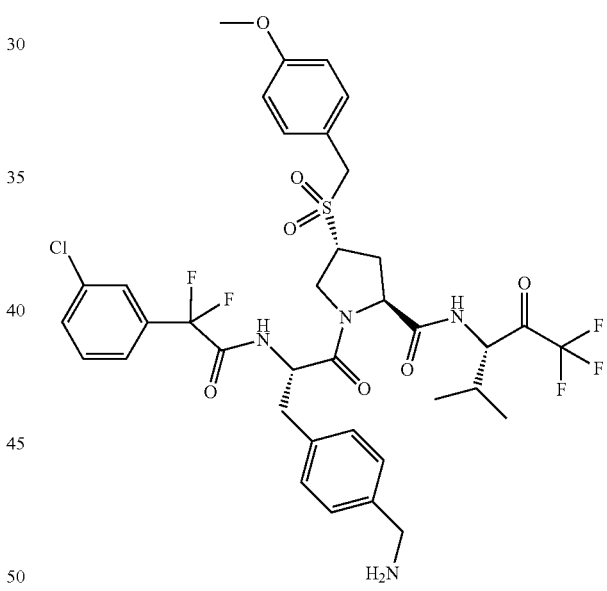

To a solution of tert-butyl N-[[4-[(2S)-2-[[2-(3-chlorophenyl)-2,2-difluoroacetyl]amino]-3-[(2S,4R)-4-[(4-methoxyphenyl)methylsulfonyl]-2-[[(3S)-1,1,1-trifluoro-4-methyl-2-oxopentan-3-yl]carbamoyl]pyrrolidin-1-yl]-3-oxopropyl]phenyl]methyl]carbamate (Example 8, 0.044 g, 0.048 mmol) in DCM (1 mL) was added TFA (0.184 mL, 2.4 mmol) and the reaction mixture was stirred at room temperature for 2.5 hours. The mixture was concentrated in vacuo. The residue was triturated in diisopropylether, filtered and further dried under high vacuum to give the title compound (0.040 g, 90%, TFA salt) as a colorless solid. MS: 815.3 (M+H$^+$).

The following examples listed in Table 2 were prepared in analogy to the procedure described for the preparation of example 21 by using the indicated starting materials.

| Ex | Name<br>Structure<br>Aspect | Reactant: compound obtained in example number indicated | MS (M + H$^+$) |
|---|---|---|---|
| 22 | (2S,4R)-1-[(2S)-3-[4-(aminomethyl)phenyl]-2-[(3-chloro-benzoyl)amino]propanoyl]-4-[(4-methoxyphenyl)methyl-sulfonyl]-N-[(3S)-1,1,1-trifluoro-4-methyl-2-oxopentan-3-yl]pyrrolidine-2-carboxamide; TFA salt<br><br>Colorless solid | Example 9 | 765.3 |
| 23 | (2S,4R)-1-[(2S)-3-[4-(aminomethyl)phenyl]-2-[[2,2-difluoro-2-[2-(trifluoromethyl)phenyl]acetyl]amino-propanoyl]-4-[(4-methoxyphenyl)methylsulfonyl]-N-[(3S)-1,1,1-trifluoro-4-methyl-2-oxopentan-3-yl]pyrrolidine-2-carboxamide; TFA salt<br><br>Colorless solid | Example 10 | 849.4 |

| Ex | Name Structure Aspect | Reactant: compound obtained in example number indicated | MS (M + H⁺) |
|---|---|---|---|
| 24 | (2S,4R)-1-[(2S)-3-[4-(aminomethyl)phenyl]-2-[[1-(4-chlorophenyl)-cyclopentanecarbonyl]aminopropanoyl]-4-[(4-methoxyphenyl)-methylsulfonyl]-N-[(3S)-1,1,1-trifluoro-4-methyl-2-oxopentan-3-yl]pyrrolidine-2-carboxamide; TFA salt 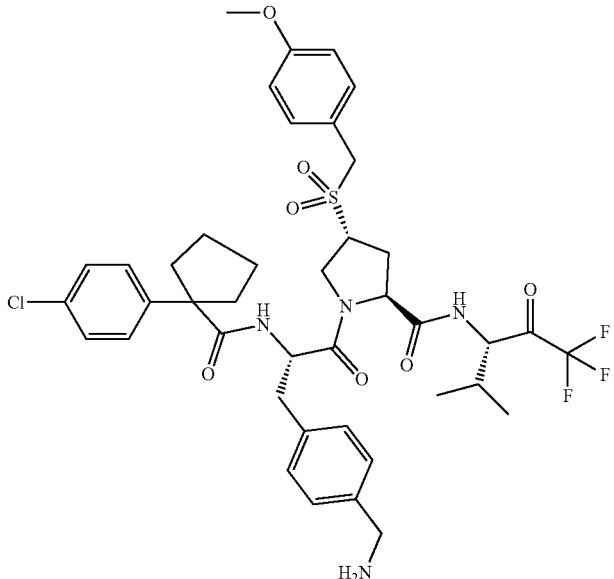 Colorless solid | Example 11 | 833.5 |

Example A

A compound of formula (I) can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| Total amount | 425 mg |

Example B

A compound of formula (I) can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| Total amount | 220.0 mg |

The invention claimed is:

1. A compound of formula (I)

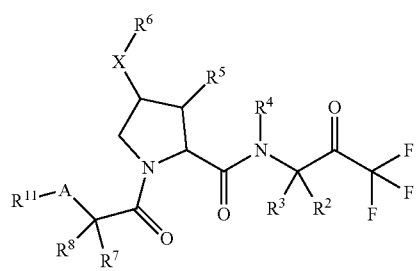

or pharmaceutically acceptable salts thereof, wherein $R^2$, $R^3$, $R^4$, $R^5$ and $R^7$ are each independently selected from
i) H,
ii) $C_{1-6}$-alkyl, and
iii) $C_{3-8}$-cycloalkyl;
X is selected from
i) —O—,
ii) —S—, and
iii) —S(O)$_2$—;
$R^6$ is selected from
i) aryl substituted with at least one of $R^{12}$, $R^{13}$ and $R^{14}$,
ii) aryl-$C_{1-6}$-alkyl substituted with at least one of $R^{12}$, $R^{13}$ and $R^{14}$,
iii) heteroaryl substituted with at least one of $R^{12}$, $R^{13}$ and $R^{14}$, and iv) heteroaryl-$C_{1-6}$-alkyl substituted with at least one of $R^{12}$, $R^{13}$ and $R^{14}$;

A is selected from
i) —O—,
ii) —$CH_2$—,
iii) —$S(O)_2NR^{10}$—, and
iv) —$C(O)NR^{10}$—;

$R^8$ is selected from
i) H, and
ii) —$CH_2R^9$;

$R^9$ is selected from
i) H,
ii) hydroxy,
iii) amino-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with at least one of $R^{15}$, $R^{16}$ and $R^{17}$,
iv) aminocarbonyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with at least one of $R^{15}$, $R^{16}$ and $R^{17}$,
v) aminocarbonyl-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with at least one of $R^{15}$, $R^{16}$ and $R^{17}$,
vi) carboxy,
vii) carboxy-$C_{1-6}$-alkyl,
viii) $C_{1-6}$-alkoxy,
ix) $C_{1-6}$-haloalkoxy,
x) $C_{1-6}$-alkoxycarbonyl,
xi) $C_{1-6}$-alkoxycarbonyl-$C_{1-6}$-alkyl,
xii) $C_{3-8}$-cycloalkyl,
xiii) aryl substituted with at least one of $R^{15}$, $R^{16}$ and $R^{17}$,
xiv) aryl-$C_{1-6}$-alkyl substituted with at least one of $R^{15}$, $R^{16}$ and $R^{17}$,
xv) aryl-$C_{1-6}$-alkoxy substituted with at least one of $R^{15}$, $R^{16}$ and $R^{17}$,
xvi) heteroaryl substituted with at least one of $R^{15}$, $R^{16}$ and $R^{17}$,
xvii) heteroaryl-$C_{1-6}$-alkyl substituted with at least one of $R^{15}$, $R^{16}$ and $R^{17}$, and
xviii) heteroaryl-$C_{1-6}$-alkoxy substituted with at least one of $R^{15}$, $R^{16}$ and $R^{17}$
xix) heterocycloalkyl substituted with at least one of $R^{15}$, $R^{16}$ and $R^{17}$,
xx) heterocycloalkyl-$C_{1-6}$-alkyl substituted with at least one of $R^{15}$, $R^{16}$ and $R^{17}$,
xxi) heterocycloalkyl-$C_{1-6}$-alkoxy substituted with at least one of $R^{15}$, $R^{16}$ and $R^{17}$, and
xxii) $C_{1-6}$-alkylsilyloxy;

$R^{10}$ is H;

$R^{11}$ is selected from
i) amino-$C_{1-6}$-alkyl substituted on the nitrogen atom by at least one of $R^{21}$ and $R^{22}$,
ii) $C_{3-8}$-cycloalkyl substituted with at least one of $R^{18}$, $R^{19}$ and $R^{20}$,
iii) $C_{3-8}$-cycloalkyl-$C_{1-6}$-alkyl substituted with at least one of $R^{18}$, $R^{19}$ and $R^{20}$,
iv) $C_{3-8}$-cycloalkyl(halo)-$C_{1-6}$-alkyl substituted with at least one of $R^{18}$, $R^{19}$ and $R^{20}$,
v) aryl substituted with at least one of $R^{18}$, $R^{19}$ and $R^{20}$,
vi) aryl-$C_{1-6}$-alkyl substituted with at least one of $R^{18}$, $R^{19}$ and $R^{20}$,
vii) aryl-$C_{3-8}$-cycloalkyl substituted with at least one of $R^{18}$, $R^{19}$ and $R^{20}$,
viii) aryl-heterocycloalkyl substituted with at least one of $R^{18}$, $R^{19}$ and $R^{20}$
ix) aryl(halo)-$C_{1-6}$-alkyl substituted with at least one of $R^{18}$, $R^{19}$ and $R^{20}$,
x) aryl(halo)-$C_{3-8}$-cycloalkyl substituted with at least one of $R^{18}$, $R^{19}$ and $R^{20}$,
xi) aryl(halo)-heterocycloalkyl substituted with at least one of $R^{18}$, $R^{19}$ and $R^{20}$,
xii) aryloxy-$C_{1-6}$-alkyl substituted with at least one of $R^{18}$, $R^{19}$ and $R^{20}$,
xiii) aryloxy-$C_{3-8}$-cycloalkyl substituted with at least one of $R^{18}$, $R^{19}$ and $R^{20}$,
xiv) aryloxy-heterocycloalkyl substituted with at least one of $R^{18}$, $R^{19}$ and $R^{20}$,
xv) aryloxy(halo)-$C_{3-8}$-cycloalkyl substituted with at least one of $R^{18}$, $R^{19}$ and $R^{20}$,
xvi) aryloxy(halo)-heterocycloalkyl substituted with at least one of $R^{18}$, $R^{19}$ and $R^{20}$
xvii) aryloxy(halo)-$C_{1-6}$-alkyl,
xviii) heterocycloalkyl substituted with at least one of $R^{18}$, $R^{19}$ and $R^{20}$,
xix) heterocycloalkyl-$C_{1-6}$-alkyl substituted with at least one of $R^{18}$, $R^{19}$ and $R^{20}$,
xx) heterocycloalkyl-$C_{3-8}$-cycloalkyl substituted with at least one of $R^{18}$, $R^{19}$ and $R^{20}$,
xxi) heterocycloalkyl(halo)-$C_{3-8}$-cycloalkyl substituted with at least one of $R^{18}$, $R^{19}$ and $R^{20}$,
i) heterocycloalkyl(halo)-$C_{1-6}$-alkyl substituted with at least one of $R^{18}$, $R^{19}$ and $R^{20}$,
ii) heteroaryl substituted with at least one of $R^{18}$, $R^{19}$ and $R^{20}$,
iii) heteroaryl-$C_{1-6}$-alkyl substituted with at least one of $R^{18}$, $R^{19}$ and $R^{20}$,
iv) heteroaryl-$C_{3-8}$-cycloalkyl substituted with at least one of $R^{18}$, $R^{19}$ and $R^{20}$,
v) heteroaryl(halo)-$C_{3-8}$-cycloalkyl substituted with at least one of $R^{18}$, $R^{19}$ and $R^{20}$,
vi) heteroaryl(halo)-$C_{1-6}$-alkyl substituted with at least one of $R^{18}$, $R^{19}$ and $R^{20}$,
vii) heteroaryloxy-$C_{1-6}$-alkyl substituted with at least one of $R^{18}$, $R^{19}$ and $R^{20}$,
viii) heteroaryloxy-$C_{3-8}$-cycloalkyl substituted with at least one of $R^{18}$, $R^{19}$ and $R^{20}$,
ix) heteroaryloxy(halo)-$C_{3-8}$-cycloalkyl substituted with at least one of $R^{18}$, $R^{19}$ and $R^{20}$, and
x) heteroaryloxy(halo)-$C_{1-6}$-alkyl substituted with at least one of $R^{18}$, $R^{19}$ and $R^{20}$;

$R^{12}$, $R^{13}$, $R^{14}$, $R^{15}$, $R^{16}$, $R^{17}$, $R^{18}$, $R^{19}$ and $R^{20}$ are each independently selected from
i) H,
ii) cyano,
iii) halogen,
iv) oxo,
v) $C_{1-6}$-alkyl,
vi) amino substituted on the nitrogen atom by two substituents independently selected from H, $C_{1-6}$-alkyl, $C_{1-6}$-alkoxycarbonyl, arylcarbonyl and heteroarylcarbonyl,
vii) amino-$C_{1-6}$-alkyl substituted on the nitrogen atom by two substituents independently selected from H, $C_{1-6}$-alkyl, $C_{1-6}$-alkoxycarbonyl, arylcarbonyl and heteroaryl carbonyl, viii) $C_{1-6}$-alkyl,
ix) halo-$C_{1-6}$-alkyl,
x) $C_{3-8}$-cycloalkyl,
xi) $C_{1-6}$-alkoxycarbonyl-$C_{1-6}$-alkyl,
xii) carboxy-$C_{1-6}$-alkyl,
xiii) $C_{1-6}$-alkoxycarbonyl-$C_{1-6}$alkylaminocarbonyl-$C_{1-6}$alkyl,
xiv) carboxy-$C_{1-6}$-alkylaminocarbonyl-$C_{1-6}$alkyl,
xv) $C_{1-6}$-alkoxy,
xvi) halo-$C_{1-6}$-alkoxy,
xvii) $C_{1-6}$-alkoxycarbonyl-$C_{1-6}$-alkoxy,
xviii) carboxy-$C_{1-6}$-alkoxy,
xix) $C_{1-6}$-alkoxycarbonyl-$C_{1-6}$-alkylaminocarbonyl-$C_{1-6}$-alkoxy,
xx) carboxy-$C_{1-6}$-alkylaminocarbonyl-$C_{1-6}$-alkoxy, and
xxi) heterocycloalkyl;
and
$R^{21}$ and $R^{22}$ are each independently selected from
i) H,
ii) $C_{1-6}$-alkoxycarbonyl,
iii) carboxy-$C_{1-6}$-alkyl,
iv) arylcarbonyl, and
v) heteroarylcarbonyl;
with the proviso that N-[(1S)-1-[[(1S)-1-[(2S,4R)-4-benzyloxy-2-[(1-ethyl-3,3,3-trifluoro-2-oxo-propyl)carbamoyl]pyrrolidine-1-carbonyl]-2-methyl-propyl]carbamoyl]-2-methyl-propyl]pyrazine-2-carboxamide is excluded.

2. The compound of claim 1, or a pharmaceutically acceptable salt thereof, wherein
$R^2$ is $C_{1-6}$-alkyl;
$R^3$, $R^4$, $R^5$ and $R^7$ are each H;
X is selected from
i) —O—,
ii) —S—, and
iii) —S(O)$_2$—;
$R^6$ is phenyl-$C_{1-6}$-alkyl substituted with at least one of $R^{12}$, $R^{13}$ and $R^{14}$;
A is selected from
i) —O—,
ii) —CH$_2$—,
iii) —S(O)$_2$NR$^{10}$— and
iv) —C(O)NR$^{10}$—;
$R^8$ is selected from
i) H, and
ii) —CH$_2$R$^9$;
$R^9$ is selected from
i) H,
ii) hydroxy,
iii) $C_{1-6}$-alkoxy,
iv) phenyl substituted with at least one of $R^{15}$, $R^{16}$ and $R^{17}$, and
v) $C_{1-6}$-alkylsilyloxy;
$R^{11}$ is selected from
i) phenyl substituted with at least one of $R^{18}$, $R^{19}$ and $R^{20}$,
ii) phenyl-$C_{3-8}$-cycloalkyl substituted with at least one of $R^{18}$, $R^{19}$ and $R^{20}$,
iii) phenyl(halo)-$C_{1-6}$-alkyl substituted with at least one of $R^{18}$, $R^{19}$ and $R^{20}$, and
iv) heteroaryl substituted with at least one of $R^{18}$, $R^{19}$ and $R^{20}$, wherein heteroaryl is selected from
a. pyrazinyl,
b. pyridinyl, and
c. thiophenyl;
$R^{12}$ is selected from
i) H, and
ii) $C_{1-6}$-alkoxy, $R^{15}$ is selected from
i) H,
ii) halogen, and
iii) amino-$C_{1-6}$-alkyl substituted on the nitrogen atom by one H and one $C_{1-6}$-alkoxycarbonyl;
$R^{18}$ is selected from
i) H,
ii) halogen, and
iii) halo-$C_{1-6}$-alkyl;
and
$R^{13}$, $R^{14}$, $R^{16}$, $R^{17}$, $R^{19}$ and $R^{20}$ are each H;
with the proviso that N-[(1S)-1-[[(1S)-1-[(2S,4R)-4-benzyloxy-2-[(1-ethyl-3,3,3-trifluoro-2-oxo-propyl)carbamoyl]pyrrolidine-1-carbonyl]-2-methyl-propyl]carbamoyl]-2-methyl-propyl]pyrazine-2-carboxamide is excluded.

3. The compound of claim 1, or a pharmaceutically acceptable salt thereof, wherein $R^2$ is $C_{1-6}$-alkyl.

4. The compound of claim 1, or a pharmaceutically acceptable salt thereof, wherein $R^3$, $R^4$, $R^5$ and $R^7$ are each H.

5. The compound of claim 1, or a pharmaceutically acceptable salt thereof, wherein X is selected from
i) —O—, and
ii) —S(O)$_2$—.

6. The compound of claim 1, or a pharmaceutically acceptable salt thereof, wherein X is —O—.

7. The compound of claim 1, or a pharmaceutically acceptable salt thereof, wherein $R^6$ is phenyl-$C_{1-6}$-alkyl substituted with at least one of $R^{12}$, $R^{13}$ and $R^{14}$.

8. The compound of claim 1, or a pharmaceutically acceptable salt thereof, wherein A is selected from
i) —O—, and
ii) —CH$_2$—.

9. The compound of claim 1, or a pharmaceutically acceptable salt thereof, wherein A is —O—.

10. The compound of claim 1, or a pharmaceutically acceptable salt thereof, wherein $R^8$ is H.

11. The compound of claim 1, or a pharmaceutically acceptable salt thereof, wherein $R^9$ is selected from
i) H,
ii) hydroxy,
iii) $C_{1-6}$-alkoxy,
iv) phenyl substituted with at least one of $R^{15}$, $R^{16}$ and $R^{17}$, and
v) $C_{1-6}$-alkylsilyloxy.

12. The compound of claim 1, or a pharmaceutically acceptable salt thereof, wherein $R^9$ is phenyl substituted with at least one of $R^5$, $R^{16}$ and $R^{17}$.

13. The compound of claim 1, or a pharmaceutically acceptable salt thereof, wherein $R^{11}$ is selected from
i) phenyl substituted with at least one of $R^{18}$, $R^{19}$ and $R^{20}$,
ii) phenyl-$C_{3-8}$-cycloalkyl substituted with at least one of $R^{18}$, $R^{19}$ and $R^{20}$,
iii) phenyl(halo)-$C_{1-6}$-alkyl substituted with at least one of $R^{18}$, $R^{19}$ and $R^{20}$, and
iv) heteroaryl substituted with at least one of $R^{18}$, $R^{19}$ and $R^{20}$, wherein heteroaryl is selected from
(a) pyrazinyl,
(b) pyridinyl, and
(c) thiophenyl.

14. The compound of claim 1, or a pharmaceutically acceptable salt thereof, wherein $R^{11}$ is phenyl substituted with at least one of $R^{18}$, $R^{19}$ and $R^{20}$.

15. The compound of claim 1, or a pharmaceutically acceptable salt thereof, wherein $R^{12}$ is selected from
i) H, and
ii) $C_{1-6}$-alkoxy.

16. The compound of claim 1, or a pharmaceutically acceptable salt thereof, wherein $R^{12}$ is H.

17. The compound of claim 1, or a pharmaceutically acceptable salt thereof, wherein $R^{15}$ is selected from
i) H,
ii) halogen, and
iii) amino-$C_{1-6}$-alkyl substituted on the nitrogen atom by one H and one $C_{1-6}$-alkoxycarbonyl.

18. The compound of claim 1, or a pharmaceutically acceptable salt thereof, wherein $R^{15}$ is H.

19. The compound of claim 1, or a pharmaceutically acceptable salt thereof, wherein $R^{18}$ is selected from
i) H,
ii) halogen, and
iii) halo-$C_{1-6}$-alkyl.

20. The compound of claim 1, or a pharmaceutically acceptable salt thereof, wherein $R^{18}$ is halogen.

21. The compound of claim 1, or a pharmaceutically acceptable salt thereof, wherein $R^{13}$, $R^{14}$, $R^{16}$, $R^{17}$, $R^{19}$ and $R^{20}$ are each H.

22. The compound of claim 1, or a pharmaceutically acceptable salt thereof, wherein
$R^2$ is $C_{1-6}$-alkyl;
$R^3$, $R^4$, $R^5$ and $R^7$ are each H;
X is —O—;
$R^6$ is phenyl-$C_{1-6}$-alkyl substituted with at least one of $R^{12}$, $R^{13}$ and $R^{14}$;
A is —O—;
$R^8$ is H;
$R^9$ is phenyl substituted with at least one of $R^{15}$, $R^{16}$ and $R^{17}$;
$R^{11}$ is phenyl substituted with at least one of $R^{18}$, $R^{19}$ and $R^{20}$;
$R^{12}$, $R^{13}$, $R^{14}$, $R^{15}$, $R^{16}$, $R^{17}$, $R^{19}$ and $R^{20}$ are each H; and
$R^{18}$ is halogen.

23. A compound according to claim 1, selected from the group consisting of:
N-((S)-3-(3-chlorophenyl)-1-((2S,4R)-4-((4-methoxybenzyl)sulfonyl)-2-(((S)-1,1,1-trifluoro-4-methyl-2-oxopentan-3-yl)carbamoyl)pyrrolidin-1-yl)-1-oxopropan-2-yl)picolinamide;
N-((S)-3-(3-chlorophenyl)-1-((2S,4R)-4-((4-methoxybenzyl)sulfonyl)-2-(((S)-1,1,1-trifluoro-4-methyl-2-oxopentan-3-yl)carbamoyl)pyrrolidin-1-yl)-1-oxopropan-2-yl)pyrazine-2-carboxamide;
(2S,4R)-1-[(2S)-2-[[2-(3-chlorophenyl)-2,2-difluoroacetyl]amino]propanoyl]-4-[(4-methoxyphenyl)methylsulfonyl]-N-[(3S)-1,1,1-trifluoro-4-methyl-2-oxopentan-3-yl]pyrrolidine-2-carboxamide;
(2S,4R)-1-[(2S)-2-[[2,2-difluoro-2-[2-(trifluoromethyl)phenyl]acetyl]amino]propanoyl]-4-[(4-methoxyphenyl)methyl sulfonyl]-N-[(3S)-1,1,1-trifluoro-4-methyl-2-oxopentan-3-yl]pyrrolidine-2-carboxamide;
(2S,4R)-1-[(2S)-2-[[2-(3-chlorophenyl)-2,2-difluoroacetyl]amino]-3-methoxypropanoyl]-4-[(4-methoxyphenyl)methyl sulfonyl]-N-[(3S)-1,1,1-trifluoro-4-methyl-2-oxopentan-3-yl]pyrrolidine-2-carboxamide;
(2S,4R)-1-[(2S)-2-[[2,2-difluoro-2-[2-(trifluoromethyl)phenyl]acetyl]amino]-3-methoxypropanoyl]-4-[(4-methoxyphenyl)methylsulfonyl]-N-[(3S)-1,1,1-trifluoro-4-methyl-2-oxopentan-3-yl]pyrrolidine-2-carboxamide;
tert-butyl N-[[4-[(2S)-2-[[2-(3-chlorophenyl)-2,2-difluoroacetyl]amino]-3-[(2S,4R)-4-[(4-methoxyphenyl)methyl sulfonyl]-2-[[(3S)-1,1,1-trifluoro-4-methyl-2-oxopentan-3-yl]carbamoyl]pyrrolidin-1-yl]-3-oxopropyl]phenyl]methyl]carbamate;
tert-butyl N-[[4-[(2S)-2-[(3-chlorobenzoyl)amino]-3-[(2S,4R)-4-[(4-methoxyphenyl)methyl sulfonyl]-2-[[(3S)-1,1,1-trifluoro-4-methyl-2-oxopentan-3-yl]carbamoyl]pyrrolidin-1-yl]-3-oxopropyl]phenyl]methyl]carbamate;
tert-butyl N-[[4-[(2S)-2-[[2,2-difluoro-2-[2-(trifluoromethyl)phenyl]acetyl]amino]-3-[(2S,4R)-4-[(4-methoxyphenyl)methylsulfonyl]-2-[[(3S)-1,1,1-trifluoro-4-methyl-2-oxopentan-3-yl]carbamoyl]pyrrolidin-1-yl]-3-oxopropyl]phenyl]methyl]carbamate;
tert-butyl N-[[4-[(2S)-2-[[1-(4-chlorophenyl)cyclopentanecarbonyl]amino]-3-[(2S,4R)-4-[(4-methoxyphenyl)methyl sulfonyl]-2-[[(3S)-1,1,1-trifluoro-4-methyl-2-oxopentan-3-yl]carbamoyl]pyrrolidin-1-yl]-3-oxopropyl]phenyl]methyl]carbamate;
(2S,4R)-1-(2-(3,5-dichlorophenoxy)acetyl)-4-((4-methoxybenzyl)sulfonyl)-N-((S)-1,1,1-trifluoro-4-methyl-2-oxopentan-3-yl)pyrrolidine-2-carboxamide;
(2S,4R)-1-(2-(3,5-dichlorophenoxy)acetyl)-4-((4-methoxybenzyl)thio)-N-((R)-1,1,1-trifluoro-4-methyl-2-oxopentan-3-yl)pyrrolidine-2-carboxamide;
(2S,4R)-4-(benzyloxy)-1-(3-(3,4-dichlorophenyl)propanoyl)-N-((S)-1,1,1-trifluoro-4-methyl-2-oxopentan-3-yl)pyrrolidine-2-carboxamide;
(2S,4R)-4-(benzyloxy)-1-(2-(3,5-dichlorophenoxy)acetyl)-N-((S)-1,1,1-trifluoro-4-methyl-2-oxopentan-3-yl)pyrrolidine-2-carboxamide;
N-((S)-1-((2S,4R)-4-(benzyloxy)-2-(((S)-1,1,1-trifluoro-4-methyl-2-oxopentan-3-yl)carbamoyl)pyrrolidin-1-yl)-3-(3-chlorophenyl)-1-oxopropan-2-yl)picolinamide;
N-((S)-1-((2S,4R)-4-(benzyloxy)-2-(((S)-1,1,1-trifluoro-4-methyl-2-oxopentan-3-yl)carbamoyl)pyrrolidin-1-yl)-3-(3-chlorophenyl)-1-oxopropan-2-yl)pyrazine-2-carboxamide;
(2S,4R)-4-(benzyloxy)-1-((R)-2-(3,5-dichlorophenoxy)-3-phenylpropanoyl)-N-((S)-1,1,1-trifluoro-4-methyl-2-oxopentan-3-yl)pyrrolidine-2-carboxamide;
(2S,4R)-1-[(2S)-2-[(5-chlorothiophen-2-yl)sulfonylamino]-3-methoxypropanoyl]-4-[(4-methoxyphenyl)methyl sulfonyl]-N-[(3S)-1,1,1-trifluoro-4-methyl-2-oxopentan-3-yl]pyrrolidine-2-carboxamide;
(2S,4R)-1-[(2S)-2-[[2-(3-chlorophenyl)-2,2-difluoroacetyl]amino]-3-hydroxypropanoyl]-4-[(4-methoxyphenyl)methyl sulfonyl]-N-[(3S)-1,1,1-trifluoro-4-methyl-2-oxopentan-3-yl]pyrrolidine-2-carboxamide;
(2S,4R)-1-[(2S)-3-[4-(aminomethyl)phenyl]-2-[[2-(3-chlorophenyl)-2,2-difluoroacetyl]amino]propanoyl]-4-[(4-methoxyphenyl)methylsulfonyl]-N-[(3S)-1,1,1-trifluoro-4-methyl-2-oxopentan-3-yl]pyrrolidine-2-carboxamide;2,2,2-trifluoroacetic acid;
(2S,4R)-1-[(2S)-3-[4-(aminomethyl)phenyl]-2-[(3-chlorobenzoyl)amino]propanoyl]-4-[(4-methoxyphenyl)methyl sulfonyl]-N-[(3S)-1,1,1-trifluoro-4-methyl-2-oxopentan-3-yl]pyrrolidine-2-carboxamide;2,2,2-trifluoroacetic acid;
(2S,4R)-1-[(2S)-3-[4-(aminomethyl)phenyl]-2-[[2,2-difluoro-2-[2-(trifluoromethyl)phenyl]acetyl]amino]propanoyl]-4-[(4-methoxyphenyl)methyl sulfonyl]-N-

[(3S)-1,1,1-trifluoro-4-methyl-2-oxopentan-3-yl]
pyrrolidine-2-carboxamide;2,2,2-trifluoroacetic acid;
and
(2S,4R)-1-[(2S)-3-[4-(aminomethyl)phenyl]-2-[[1-(4-chlorophenyl)cyclopentanecarbonyl]amino]propanoyl]-4-[(4-methoxyphenyl)methyl sulfonyl]-N-[(3S)-1,1,1-trifluoro-4-methyl-2-oxopentan-3-yl]
pyrrolidine-2-carboxamide;2,2,2-trifluoroacetic acid;
or a pharmaceutically acceptable salt thereof.

24. The compound of claim 1, selected from the group consisting of:
(2S,4R)-1-(2-(3,5-dichlorophenoxy)acetyl)-4-((4-methoxybenzyl)sulfonyl)-N-((S)-1,1,1-trifluoro-4-methyl-2-oxopentan-3-yl)pyrrolidine-2-carboxamide;
(2S,4R)-4-(benzyloxy)-1-(3-(3,4-dichlorophenyl)propanoyl)-N-((S)-1,1,1-trifluoro-4-methyl-2-oxopentan-3-yl)pyrrolidine-2-carboxamide;
(2S,4R)-4-(benzyloxy)-1-(2-(3,5-dichlorophenoxy)acetyl)-N-((S)-1,1,1-trifluoro-4-methyl-2-oxopentan-3-yl)pyrrolidine-2-carboxamide; and
(2S,4R)-4-(benzyloxy)-1-((R)-2-(3,5-dichlorophenoxy)-3-phenylpropanoyl)-N-((S)-1,1,1-trifluoro-4-methyl-2-oxopentan-3-yl)pyrrolidine-2-carboxamide;
or a pharmaceutically acceptable salt thereof.

25. A process to prepare the compound of claim 1 comprising the reaction of a compound of formula (II) in oxidative conditions

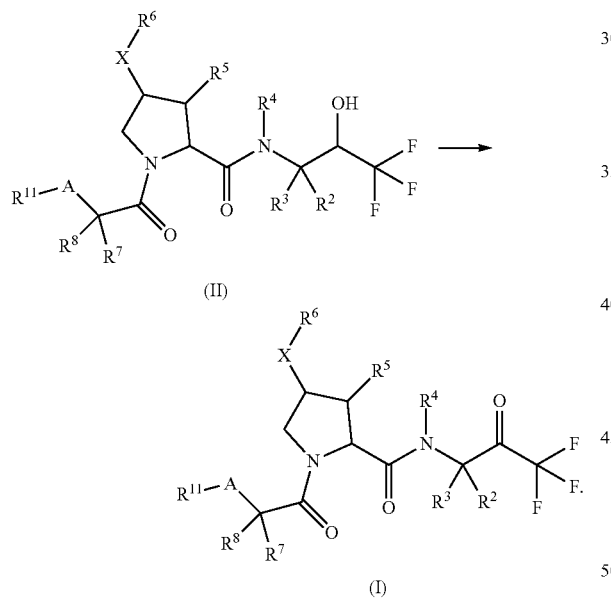

26. A pharmaceutical composition comprising the compound of claim 1, or a pharmaceutically acceptable salt thereof, and a therapeutically inert carrier.

27. A method for the treatment of an HtrA1-mediated condition selected from the group consisting of wet or dry age-related macular degeneration, geographic atrophy, diabetic retinopathy, retinopathy of prematurity and polypoidal choroidal vasculopathy, which method comprises administering to a mammal in need thereof an effective amount of a compound according to claim 1, or a pharmaceutically acceptable salt thereof.

28. The compound of claim 1, wherein said compound is manufactured according to a process comprising the reaction of a compound of formula (II) in oxidative conditions

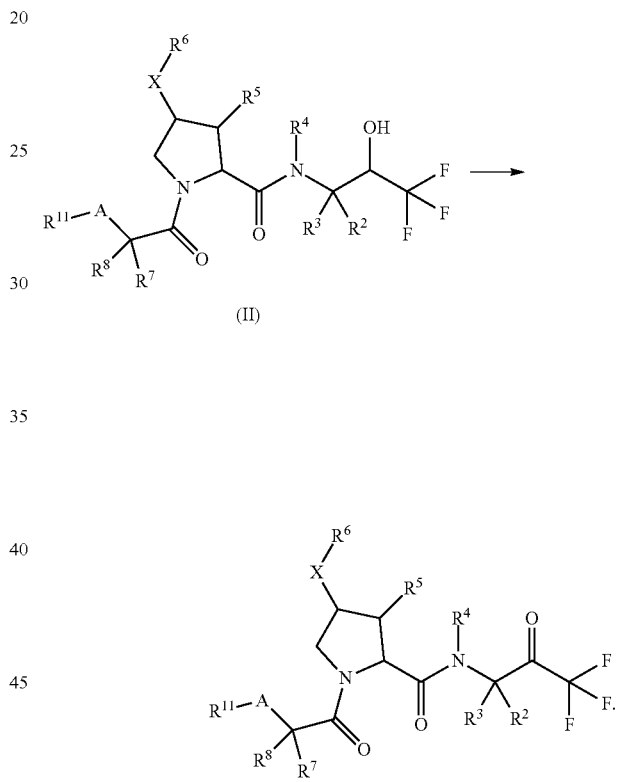

* * * * *